United States Patent
Morgan et al.

(10) Patent No.: US 10,759,721 B2
(45) Date of Patent: Sep. 1, 2020

(54) DEUTERATED CFTR POTENTIATORS

(71) Applicant: Vertex Pharmaceuticals (Europe) Limited, Abingdon, Oxfordshire (GB)

(72) Inventors: Adam J. Morgan, Lexington, MA (US); Roger D. Tung, Lexington, MA (US)

(73) Assignee: Vertex Pharmaceuticals (Europe) Limited, London (GB)

( * ) Notice: Subject to any disclaimer, the term of this patent is extended or adjusted under 35 U.S.C. 154(b) by 56 days.

(21) Appl. No.: 15/762,264

(22) PCT Filed: Sep. 23, 2016

(86) PCT No.: PCT/US2016/053323
§ 371 (c)(1),
(2) Date: Mar. 22, 2018

(87) PCT Pub. No.: WO2017/053711
PCT Pub. Date: Mar. 30, 2017

(65) Prior Publication Data
US 2020/0031776 A1    Jan. 30, 2020

Related U.S. Application Data

(60) Provisional application No. 62/232,834, filed on Sep. 25, 2015.

(51) Int. Cl.
*C07B 49/00* (2006.01)
*C07D 215/56* (2006.01)

(52) U.S. Cl.
CPC ............ *C07B 49/00* (2013.01); *C07D 215/56* (2013.01)

(58) Field of Classification Search
CPC ..................................................... C09B 49/00
See application file for complete search history.

(56) References Cited

U.S. PATENT DOCUMENTS

| | | | |
|---|---|---|---|
| 5,846,514 A | 12/1998 | Foster et al. | |
| 6,221,335 B1 | 4/2001 | Foster | |
| 6,440,710 B1 | 8/2002 | Keinan et al. | |
| 6,603,008 B1 | 8/2003 | Ando et al. | |
| 7,495,103 B2 | 2/2009 | Hadida Ruah et al. | |
| 7,517,990 B2 | 4/2009 | Ito et al. | |
| 7,553,855 B2 | 6/2009 | Young et al. | |
| 8,076,357 B2 | 12/2011 | Young et al. | |
| 8,101,767 B2 | 1/2012 | Ruah et al. | |
| 8,163,772 B2 | 4/2012 | DeMattei et al. | |
| 8,314,239 B2 | 11/2012 | Binch et al. | |
| 8,324,242 B2 | 12/2012 | Ruah et al. | |
| 8,354,427 B2 | 1/2013 | Van Goor | |
| 8,362,253 B2 | 1/2013 | DeMattei et al. | |
| 8,410,274 B2 | 4/2013 | Hurter et al. | |
| 8,436,014 B2 | 5/2013 | Zhang et al. | |
| 8,471,029 B2 | 6/2013 | Arekar et al. | |
| 8,476,442 B2 | 7/2013 | DeMattei et al. | |
| 8,507,534 B2 | 8/2013 | Keshavarz-Shokri et al. | |
| 8,513,282 B2 | 8/2013 | Binch et al. | |
| 8,552,034 B2 | 10/2013 | Verwijs et al. | |
| 8,598,205 B2 | 12/2013 | Binch et al. | |
| 8,604,203 B2 | 12/2013 | Binch et al. | |
| 8,614,325 B2 | 12/2013 | Yang et al. | |
| 8,614,327 B2 | 12/2013 | Sheth et al. | |
| 8,623,894 B2 | 1/2014 | DeMattei et al. | |
| 8,629,162 B2 | 1/2014 | Hadida-Ruah et al. | |
| 8,653,103 B2 | 2/2014 | Keshavarz-Shokri et al. | |
| 8,674,108 B2 | 3/2014 | Luisi et al. | |
| 8,741,925 B2 | 6/2014 | Hadida-Ruah et al. | |

(Continued)

FOREIGN PATENT DOCUMENTS

| | | |
|---|---|---|
| CN | 1148843 A | 4/1997 |
| CN | 101765582 A | 6/2010 |

(Continued)

OTHER PUBLICATIONS

Noel et al. "Synthese Du Tertiobutyl-2 dinitro-4,6 Phenol Noyau-14C (U) ("Dinoterbe" Noyau-14C)" Journal of Labelled Compounds and Radiopharmaceuticals, 1980, vol. 17, No. 2, pp. 215-222.*
Baillie, T. A. (1981) "The Use of Stable Isotopes in Pharmacological Research" *Pharmacological Reviews*, 33(2):81-132.
Blake, M.I. et al. (1975) "Studies with Deuterated Drugs" *J Pharm Sci*, 64(3):367-391.
Bombieri, C. et al., "Recommendations for the classification of diseases of CFTR-related disorders," *J Cyst Fibros* 10:2 S86-S102 (2011).
Browne, T. R. (1998) "Stable Isotope Techniques in Early Drug Development: An Economic Evaluation" *J Clin Pharmacol*, 38: 213-220.

(Continued)

*Primary Examiner* — Joseph R Kosack
(74) *Attorney, Agent, or Firm* — Finnegan, Henderson, Farabow, Garrett & Dunner LLP.

(57) ABSTRACT

This invention relates to compounds of Formula I:

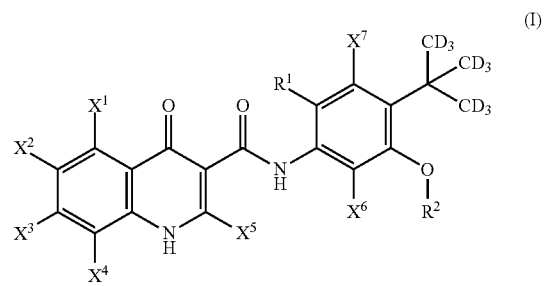

and pharmaceutically acceptable salts thereof, wherein each X and each R is defined within. This invention also provides compositions comprising a compound of this invention and the use of such compositions in methods of treating diseases and conditions that are beneficially treated by administering a CFTR potentiator.

1 Claim, No Drawings

(56) References Cited

U.S. PATENT DOCUMENTS

| | | |
|---|---|---|
| 8,754,224 B2 | 6/2014 | Hurter et al. |
| 8,765,957 B2 | 7/2014 | DeMattei et al. |
| 8,785,476 B2 | 7/2014 | Arekar et al. |
| 8,785,640 B2 | 7/2014 | Binch et al. |
| 8,796,308 B2 | 8/2014 | Yang et al. |
| 8,802,700 B2 | 8/2014 | Sheth et al. |
| 8,829,204 B2 | 9/2014 | Hadida-Ruah et al. |
| 8,835,639 B2 | 9/2014 | DeMattei et al. |
| 8,846,718 B2 | 9/2014 | Keshavarz-Shokri et al. |
| 8,865,902 B2 | 10/2014 | Morgan |
| 8,883,206 B2 | 11/2014 | Dokou et al. |
| 8,969,382 B2 | 3/2015 | Binch et al. |
| 9,045,425 B2 | 6/2015 | Luisi et al. |
| 9,090,619 B2 | 7/2015 | Hadida-Ruah et al. |
| 9,139,530 B2 | 9/2015 | Hurter et al. |
| 9,150,552 B2 | 10/2015 | Keshavarz-Shokri et al. |
| 9,181,192 B2 | 11/2015 | Morgan |
| 9,241,934 B2 | 1/2016 | Verwijs et al. |
| 9,371,287 B2 | 6/2016 | DeMattei et al. |
| 9,434,717 B2 | 9/2016 | Keshavarz-Shokri et al. |
| 9,512,079 B2 | 12/2016 | Morgan |
| 9,670,163 B2 | 6/2017 | Hurter et al. |
| 9,701,639 B2 | 7/2017 | Strohmeier et al. |
| 9,751,839 B2 | 9/2017 | Demattei et al. |
| 9,840,499 B2 | 12/2017 | Keshavarz-Shokri et al. |
| 9,931,334 B2 | 4/2018 | Hurter et al. |
| 10,047,053 B2 | 8/2018 | Morgan |
| 10,272,046 B2 | 4/2019 | Dokou et al. |
| 10,479,766 B2 | 11/2019 | Morgan et al. |
| 10,537,565 B2 | 1/2020 | Hurter et al. |
| 2007/0082929 A1 | 4/2007 | Gant et al. |
| 2007/0197695 A1 | 8/2007 | Potyen et al. |
| 2008/0103122 A1 | 5/2008 | Veltri |
| 2009/0105272 A1 | 4/2009 | Grootenhuis et al. |
| 2009/0246820 A1 | 10/2009 | Singh et al. |
| 2010/0074949 A1 | 3/2010 | Rowe et al. |
| 2010/0256184 A1 | 10/2010 | Rowe et al. |
| 2011/0064811 A1 | 3/2011 | Hurter et al. |
| 2011/0098311 A1 | 4/2011 | Van Goor et al. |
| 2011/0257223 A1 | 10/2011 | Van Goor et al. |
| 2011/0288122 A1 | 11/2011 | Van Goor et al. |
| 2012/0064157 A1 | 3/2012 | Doukou et al. |
| 2012/0122921 A1 | 5/2012 | DeMattei et al. |
| 2012/0122922 A1 | 5/2012 | Young et al. |
| 2012/0220625 A1 | 8/2012 | Rowe et al. |
| 2012/0258983 A1 | 10/2012 | Rowe et al. |
| 2013/0018071 A1 | 1/2013 | Arekar et al. |
| 2013/0090354 A1 | 4/2013 | Van Goor et al. |
| 2013/0131107 A1 | 5/2013 | Van Goor et al. |
| 2013/0143919 A1 | 6/2013 | Van Goor et al. |
| 2013/0158071 A1 | 6/2013 | Van Goor et al. |
| 2013/0224293 A1 | 8/2013 | Dokou et al. |
| 2013/0231368 A1 | 9/2013 | Zhang et al. |
| 2013/0303484 A1 | 11/2013 | Grootenhuis et al. |
| 2013/0331567 A1 | 12/2013 | Hadida-Ruah et al. |
| 2014/0023706 A1 | 1/2014 | Verwijs et al. |
| 2014/0112988 A1 | 4/2014 | Rowe et al. |
| 2014/0142138 A1 | 5/2014 | Van Goor et al. |
| 2014/0155431 A1 | 6/2014 | Hadida-Ruah et al. |
| 2014/0163011 A1 | 6/2014 | Hadida-Ruah et al. |
| 2014/0163068 A1 | 6/2014 | Verwijs et al. |
| 2014/0221424 A1 | 8/2014 | Zha |
| 2014/0243289 A1 | 8/2014 | Grootenhuis et al. |
| 2014/0303204 A1 | 10/2014 | Binch et al. |
| 2014/0303205 A1 | 10/2014 | Yang et al. |
| 2014/0315948 A1 | 10/2014 | Rowe et al. |
| 2014/0323521 A1 | 10/2014 | Van Goor et al. |
| 2014/0329855 A1 | 11/2014 | Arekar et al. |
| 2014/0343098 A1 | 11/2014 | Sheth et al. |
| 2014/0350281 A1 | 11/2014 | DeMattei et al. |
| 2015/0010628 A1 | 1/2015 | Dokou et al. |
| 2015/0024047 A1 | 1/2015 | Dokou et al. |
| 2015/0031722 A1 | 1/2015 | Hadida-Ruah et al. |
| 2015/0080431 A1 | 3/2015 | Van Goor et al. |
| 2015/0246031 A1 | 9/2015 | Dokou et al. |
| 2015/0293078 A1 | 10/2015 | Singh et al. |
| 2015/0315186 A2 | 11/2015 | Hadida-Ruah et al. |
| 2015/0336898 A1 | 11/2015 | Grootenhuis et al. |
| 2016/0022664 A2 | 1/2016 | Van Goor et al. |
| 2016/0022665 A2 | 1/2016 | Van Goor et al. |
| 2016/0067239 A9 | 3/2016 | Van Goor et al. |
| 2016/0221952 A1 | 8/2016 | Yang et al. |
| 2016/0303096 A1 | 10/2016 | Verwijs et al. |
| 2016/0318931 A1 | 11/2016 | Hadida Ruah et al. |
| 2016/0324846 A1 | 11/2016 | Verwijs et al. |
| 2017/0087144 A1 | 3/2017 | Rowe et al. |
| 2017/0137383 A1 | 5/2017 | Morgan |
| 2018/0125838 A1 | 5/2018 | Uttamsingh |
| 2018/0127398 A1 | 5/2018 | Keshavarz-Shokri et al. |
| 2018/0353500 A1 | 12/2018 | Braman |
| 2019/0070162 A1 | 3/2019 | Hurter et al. |
| 2019/0144450 A1 | 5/2019 | Hadida Ruah et al. |
| 2019/0274959 A1 | 9/2019 | Dokou et al. |
| 2020/0031776 A1 | 1/2020 | Morgan et al. |

FOREIGN PATENT DOCUMENTS

| | | |
|---|---|---|
| CN | 102234275 A | 11/2011 |
| JP | H09-510717 A | 10/1997 |
| JP | 2005-529969 A | 10/2005 |
| JP | 2005-532285 A | 10/2005 |
| JP | 2008-504291 A | 2/2008 |
| JP | 2010-539166 A | 12/2010 |
| WO | WO 95/26325 A2 | 10/1995 |
| WO | WO 2003/084954 A1 | 10/2003 |
| WO | WO 2004/000854 A1 | 12/2003 |
| WO | WO 2006/002421 A2 | 1/2006 |
| WO | WO 2007/079139 A2 | 7/2007 |
| WO | WO 2007/118651 A1 | 10/2007 |
| WO | WO 2008/134525 A1 | 11/2008 |
| WO | WO 2009/035652 A1 | 3/2009 |
| WO | WO 2010/028015 A2 | 3/2010 |
| WO | WO 2011/072241 A1 | 6/2011 |
| WO | WO 2011/116397 A1 | 9/2011 |
| WO | WO 2012/158885 A1 | 11/2012 |
| WO | WO 2014/078842 A1 | 5/2014 |
| WO | WO 2015/063041 A1 | 5/2015 |
| WO | WO 2017/053455 A1 | 3/2017 |
| WO | WO 2017/053711 A2 | 3/2017 |
| WO | WO 2018/080591 A1 | 5/2018 |

OTHER PUBLICATIONS

Buck, Marcia L., "Ivacaftor for the Treatment of Patients with Cystic Fibrosis and the G551D-CFTR Mutation", Pediatric Pharmacotherapy, 18(4), four pages, Apr. 2012.

Buteau, K.C. (Jan. 2009) "Deuterated Drugs: Unexpectedly Nonobvious?" *Journal of High Technology Law*, 10(1):22-74.

Chen, Y. et al. (2011) "Drug-Drug Interaction between VX-770 and CYP3A Modulators" Abstracts of the 40th Annual Meeting of the American College of Clinical Pharmacology, Sep. 11-13, 2011, Chicago, Illinois. *J Clin Pharmacol*, 51:1348, Abstract 1122989.

Cherrah, Y. et al. (1987) "Study of Deuterium Isotope Effects on Protein Binding by Gas Chromatography/Mass Spectrometry. Caffeine and Deuterated Isotopomers" *Biomedical and Environmental Mass Spectrometry*, 14: 653-657.

Concert Pharmaceuticals, Inc. (2007) "Precision Deuterium Chemistry Backgrounder" [online]. Retrieved from the Internet: URL:http://www.webcitation.org/5e81SGCnI [retrieved on May 12, 2011] (6 pages).

Condren, Michelle E., et al., "Ivacaftor: A Novel Gene-Based Therapeutic Approach for Cystic Fibrosis", J Pediatr Pharmacol Ther 2013; 18(1):8-13.

Database PUBCHEM, Substance Record for SID 163435970. Create Date: Jun. 10, 2013. [retrieved on Oct. 24, 2016]. Retrieved from the Internet: https://pubchem.ncbi.nlm.nih.gov/substance/1634359070.

Dyck, L. E. et al. (1986) "Effects of Deuterium Substitution on the Catabolism of β-Phenylethylamine: An in Vivo Study" *J Neurochem*, 46(2): 399-404.

(56) References Cited

OTHER PUBLICATIONS

European Medicines Agency. Kalydeco 150 mg film-coated tablets: summary of product characteristics; 2013.

European Patent Application No. 12725197: Response to Communication dated Jan. 7, 2014. European Patent Register, Jul. 15, 2014 (12 pages).

Fisher, M.B. et al. (2006) "The Complexities Inherent in Attempts to Decrease Drug Clearance by Blocking Sites of CYP-Mediated Metabolism" *Curr Opin Drug Discov Devel*, 9(1):101-109.

Fohner, Alison E., "PharmGKB summary: ivacaftor pathway, pharmacokinetics/pharmacodynamics", Pharmacogenet Genomics, Jan. 2017; 27(1):39-42.

Foster, A.B. (1984) "Deuterium Isotope Effects in Studies of Drug Metabolism" *Trends in Pharmacological Sciences*, 5:524-527.

Foster, A.B. (1985) "Deuterium Isotope Effects in the Metabolism of Drugs and Xenobiotics: Implications for Drug Design" *Advances in Drug Research*, 14:1-40.

Fukuto, J.M. et al. (1991) "Determination of the Mechanism of Demethylenation of (Methylenedioxy)phenyl Compounds by Cytochrome P450 Using Deuterium Isotope Effects" *J Med Chem*, 34:2871-2876.

Gouyette, A. (1988) "Synthesis of Deuterium-labelled Elliptinium and its Use in Metabolic Studies" *Biomedical and Environmental Mass Spectrometry*, 15:243-247.

Hadida, S. et al. (2014) "Discovery of N-(2,4-Di-tert-butyl-5-hydroxyphenyl)-4-oxo-1,4-dihydroguinoline-3-carboxamide (VX-770, Ivacaftor), a Potent and Orally Bioavailable CFTR Potentiator" *J Med Chem*, 57:9776-9795.

Haskins, N. J. (1982) "The Application of Stable Isotopes in Biomedical Research" *Biomedical Mass Spectrometry*, 9(7): 269-277.

Honma, S. et al. (1987) "The metabolism of roxatidine acetate hydrochloride. Liberation of deuterium from the piperidine ring during hydroxylation" *Drug Metabolism and Disposition*, 15(4):551-559.

International Preliminary Report on Patentability issued in International Patent Application PCT/US2016/052922; dated Apr. 5, 2018.

International Preliminary Report on Patentability issued in International Patent Application PCT/US2016/053323; dated Apr. 5, 2018.

International Search Report and Written Opinion issued in International Patent Application PCT/US2012/038297; dated Jul. 13, 2012 (11 pages).

International Search Report and Written Opinion issued in International Patent Application PCT/US2013/070748; dated Jan. 17, 2014 (12 pages).

International Search Report and Written Opinion issued in International Patent Application PCT/US2016/052922; dated Dec. 8, 2016 (8 pages).

International Search Report and Written Opinion issued in International Patent Application PCT/US2016/053323; dated Mar. 9, 2017 (10 pages).

International Search Report and Written Opinion issued in International Patent Application PCT/US2017/029920; dated Jul. 13, 2017 (8 pages).

Ivacaftor FDA Medical Review, Nov. 2011, pp. 1-109.

Kushner, D.J. et al. (1999) "Pharmacological Uses and Perspectives of Heavy Water and Deuterated Compounds" *Can J Physiol Pharmacol*, 77:79-88.

Nguyen et al. (Research article abstracts from the 10th international Issx meeting, 2013, p. 309, "Deuterated isotopologs of ivacaftor have improved metabolism and pharmacokinetic properties".

O'Driscoll, C. (Mar. 9, 2009) "Heavyweight Drugs. Swapping Selected Hydrogen Atoms for Deuterium Could Be a Fast Route to Making Safer, Longer Lasting Drugs" *Chemistry & Industry*, pp. 24-26.

Pieniaszek, H.J. et al. (1999) "Moricizine Bioavailability via Simultaneous, Dual, Stable Isotope Administration: Bioequivalence Implications" *J Clin Pharmacol*, 39:817-825.

Sanderson, K. (2009) "Big interest in heavy drugs. The drug industry is seeking profits by modifying hydrogen in existing medications" *Nature*, 458:269.

Schellekens, R. et al. (2011) "Applications of stable isotopes in clinical pharmacology" *British Journal of Clinical Pharmacology*, 72(6):879-897.

Shao, L. et al. (2010) "The kinetic isotope effect in the search for deuterated drugs" *Drug News Perspect*, 23(6):398-404.

Tonn, G.R. et al. (1993) "Simultaneous Analysis of Diphenhydramine and a Stable Isotope Analog ($^2H_{10}$) Diphenhydramine Using Capillary Gas Chromatography with Mass Selective Detection in Biological Fluids from Chronically Instrumented Pregnant Ewes" *Biological Mass Spectrometry*, 22:633-642.

U.S. FDA, Center for Drug Evaluation and Research: IVACAFTOR (VX-770), Application No. NDA 203-188Orig1s000, Clinical Pharmacology and Biopharmaceutics Review(s), Reference ID: 3073697; Jan. 18, 2012 (102 pages).

Uttamsingh, V. et al. (2016) "WS13.6 CTP-656 tablet confirmed superiority of pharmacokinetic profile relative to Kalydeco in Phase I clinical studies" *Journal of Cystic Fibrosis*, 15:S22.

Van Goor, F. et al. (2009) "Rescue of CF airway epithelial cell function in vitro by a CFTR potentiator, VX-770" *PNAS*, 106(44):18825-18830.

Vertex Pharmaceuticals, Inc. (Jan. 2012) KALYDECO™ (ivacaftor) Tablets. Highlights of Prescribing Information (13 pages).

Wang, Shizhen (Ed.) "Use of Nuclear Technology in Drug Study" Chapter 21 in: *Molecular Nuclear Medicine*. 1st Ed. Beijing, China: Peking Union Medical College Press, Apr. 30, 2004; pp. 416-418 (Chinese).

Wolen, R.L. (1986) "The Application of Stable Isotopes to Studies of Drug Bioavailability and Bioequivalence" *J Clin Pharmacol*, 26:419-424.

\* cited by examiner

DEUTERATED CFTR POTENTIATORS

RELATED APPLICATIONS

The application is national stage application under 35 U.S.C. § 371 of international application number PCT/US2016/053323, filed Sep. 23, 2016, which designated the U.S. and claims the benefit of and priority to U.S. Provisional Patent Application No. 62/232,834, filed Sep. 25, 2015, the contents of which is incorporated herein by reference in its entirety.

BACKGROUND OF THE INVENTION

Many current medicines suffer from poor absorption, distribution, metabolism and/or excretion (ADME) properties that prevent their wider use or limit their use in certain indications. Poor ADME properties are also a major reason for the failure of drug candidates in clinical trials. While formulation technologies and prodrug strategies can be employed in some cases to improve certain ADME properties, these approaches often fail to address the underlying ADME problems that exist for many drugs and drug candidates. One such problem is rapid metabolism that causes a number of drugs, which otherwise would be highly effective in treating a disease, to be cleared too rapidly from the body. A possible solution to rapid drug clearance is frequent or high dosing to attain a sufficiently high plasma level of drug. This, however, introduces a number of potential treatment problems such as poor patient compliance with the dosing regimen, side effects that become more acute with higher doses, and increased cost of treatment. A rapidly metabolized drug may also expose patients to undesirable toxic or reactive metabolites.

Another ADME limitation that affects many medicines is the formation of toxic or biologically reactive metabolites. As a result, some patients receiving the drug may experience toxicities, or the safe dosing of such drugs may be limited such that patients receive a suboptimal amount of the active agent. In certain cases, modifying dosing intervals or formulation approaches can help to reduce clinical adverse effects, but often the formation of such undesirable metabolites is intrinsic to the metabolism of the compound.

In some select cases, a metabolic inhibitor will be co-administered with a drug that is cleared too rapidly. Such is the case with the protease inhibitor class of drugs that are used to treat HIV infection. The FDA recommends that these drugs be co-dosed with ritonavir, an inhibitor of cytochrome P450 enzyme 3A4 (CYP3A4), the enzyme typically responsible for their metabolism (see Kempf, D. J. et al., Antimicrobial agents and chemotherapy, 1997, 41(3): 654-60). Ritonavir, however, causes adverse effects and adds to the pill burden for HIV patients who must already take a combination of different drugs. Similarly, the CYP2D6 inhibitor quinidine has been added to dextromethorphan for the purpose of reducing rapid CYP2D6 metabolism of dextromethorphan in a treatment of pseudobulbar affect. Quinidine, however, has unwanted side effects that greatly limit its use in potential combination therapy (see Wang, L et al., Clinical Pharmacology and Therapeutics, 1994, 56(6 Pt 1): 659-67; and FDA label for quinidine at www.accessdata.fda.gov).

In general, combining drugs with cytochrome P450 inhibitors is not a satisfactory strategy for decreasing drug clearance. The inhibition of a CYP enzyme's activity can affect the metabolism and clearance of other drugs metabolized by that same enzyme. CYP inhibition can cause other drugs to accumulate in the body to toxic levels.

A potentially attractive strategy for improving a drug's metabolic properties is deuterium modification. In this approach, one attempts to slow the CYP-mediated metabolism of a drug or to reduce the formation of undesirable metabolites by replacing one or more hydrogen atoms with deuterium atoms. Deuterium is a safe, stable, non-radioactive isotope of hydrogen. Compared to hydrogen, deuterium forms stronger bonds with carbon. In select cases, the increased bond strength imparted by deuterium can positively impact the ADME properties of a drug, creating the potential for improved drug efficacy, safety, and/or tolerability. At the same time, because the size and shape of deuterium are essentially identical to those of hydrogen, replacement of hydrogen by deuterium would not be expected to affect the biochemical potency and selectivity of the drug as compared to the original chemical entity that contains only hydrogen.

Over the past 35 years, the effects of deuterium substitution on the rate of metabolism have been reported for a very small percentage of approved drugs (see, e.g., Blake, M I et al, J Pharm Sci, 1975, 64:367-91; Foster, A B, Adv Drug Res, 1985, 14:1-40 ("Foster"); Kushner, D J et al, Can J Physiol Pharmacol, 1999, 79-88; Fisher, M B et al, Curr Opin Drug Discov Devel, 2006, 9:101-09 ("Fisher")). The results have been variable and unpredictable. For some compounds deuteration caused decreased metabolic clearance in vivo. For others, there was no change in metabolism. Still others demonstrated increased metabolic clearance. The variability in deuterium effects has also led experts to question or dismiss deuterium modification as a viable drug design strategy for inhibiting adverse metabolism (see Foster at p. 35 and Fisher at p. 101).

The effects of deuterium modification on a drug's metabolic properties are not predictable even when deuterium atoms are incorporated at known sites of metabolism. Only by actually preparing and testing a deuterated drug can one determine if and how the rate of metabolism will differ from that of its non-deuterated counterpart. See, for example, Fukuto et al. (J. Med. Chem., 1991, 34, 2871-76). Many drugs have multiple sites where metabolism is possible. The site(s) where deuterium substitution is required and the extent of deuteration necessary to see an effect on metabolism, if any, will be different for each drug.

This invention relates to novel derivatives of ivacaftor, and pharmaceutically acceptable salts thereof. This invention also provides compositions comprising a compound of this invention and the use of such compositions in methods of treating diseases and conditions that are beneficially treated by administering a CFTR (cystic fibrosis transmembrane conductance regulator) potentiator.

Ivacaftor, also known as VX-770 and by the chemical name, N-(2,4-di-tert-butyl-5-hydroxyphenyl)-4-oxo-1,4-dihydroquinoline-3-carboxamide, acts as a CFTR potentiator. Results from phase III trials of VX-770 in patients with cystic fibrosis carrying at least one copy of the G551D-CFTR mutation demonstrated marked levels of improvement in lung function and other key indicators of the disease including sweat chloride levels, likelihood of pulmonary exacerbations and body weight. VX-770 is also currently in phase II clinical trials in combination with VX-809 (a CFTR corrector) for the oral treatment of cystic fibrosis patients who carry the more common ΔF508-CFTR mutation. VX-770 was granted fast track designation and orphan drug designation by the FDA in 2006 and 2007, respectively.

Potent analogs of VX-770 have also been described (Hadida, S et al, J Med Chem, 2014, 57, 9776-95), but the most potent of those analogs is metabolized much faster than VX-770.

Despite the beneficial activities of VX-770 and the potent analogs thereof, there is a continuing need for new compounds to treat the aforementioned diseases and conditions.

Definitions

The term "treat" means decrease, suppress, attenuate, diminish, arrest, or stabilize the development or progression of a disease (e.g., a disease or disorder delineated herein), lessen the severity of the disease or improve the symptoms associated with the disease.

"Disease" means any condition or disorder that damages or interferes with the normal function of a cell, tissue, or organ.

It will be recognized that some variation of natural isotopic abundance occurs in a synthesized compound depending upon the origin of chemical materials used in the synthesis. Thus, a preparation of VX-770 will inherently contain small amounts of deuterated isotopologues. The concentration of naturally abundant stable hydrogen and carbon isotopes, notwithstanding this variation, is small and immaterial as compared to the degree of stable isotopic substitution of compounds of this invention. See, for instance, Wada, E et al., Seikagaku, 1994, 66:15; Gannes, L Z et al., Comp Biochem Physiol Mol Integr Physiol, 1998, 119:725.

In the compounds of this invention any atom not specifically designated as a particular isotope is meant to represent any stable isotope of that atom. Unless otherwise stated, when a position is designated specifically as "H" or "hydrogen", the position is understood to have hydrogen at its natural abundance isotopic composition. Also unless otherwise stated, when a position is designated specifically as "D" or "deuterium", the position is understood to have deuterium at an abundance that is at least 3000 times greater than the natural abundance of deuterium, which is 0.015% (i.e., at least 45% incorporation of deuterium).

The term "isotopic enrichment factor" as used herein means the ratio between the isotopic abundance and the natural abundance of a specified isotope.

In other embodiments, a compound of this invention has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

The term "isotopologue" refers to a species in which the chemical structure differs from a specific compound of this invention only in the isotopic composition thereof.

The term "compound," when referring to a compound of this invention, refers to a collection of molecules having an identical chemical structure, except that there may be isotopic variation among the constituent atoms of the molecules. Thus, it will be clear to those of skill in the art that a compound represented by a particular chemical structure containing indicated deuterium atoms, will also contain lesser amounts of isotopologues having hydrogen atoms at one or more of the designated deuterium positions in that structure. The relative amount of such isotopologues in a compound of this invention will depend upon a number of factors including the isotopic purity of deuterated reagents used to make the compound and the efficiency of incorporation of deuterium in the various synthesis steps used to prepare the compound.

The invention also provides salts of the compounds of the invention. A salt of a compound of this invention is formed between an acid and a basic group of the compound, such as an amino functional group, or a base and an acidic group of the compound, such as a carboxyl functional group. According to another embodiment, the compound is a pharmaceutically acceptable acid addition salt.

The term "pharmaceutically acceptable," as used herein, refers to a component that is, within the scope of sound medical judgment, suitable for use in contact with the tissues of humans and other mammals without undue toxicity, irritation, allergic response and the like, and are commensurate with a reasonable benefit/risk ratio. A "pharmaceutically acceptable salt" means any non-toxic salt that, upon administration to a recipient, is capable of providing, either directly or indirectly, a compound of this invention. A "pharmaceutically acceptable counterion" is an ionic portion of a salt that is not toxic when released from the salt upon administration to a recipient.

Acids commonly employed to form pharmaceutically acceptable salts include inorganic acids such as hydrogen bisulfide, hydrochloric acid, hydrobromic acid, hydroiodic acid, sulfuric acid and phosphoric acid, as well as organic acids such as para-toluenesulfonic acid, salicylic acid, tartaric acid, bitartaric acid, ascorbic acid, maleic acid, besylic acid, fumaric acid, gluconic acid, glucuronic acid, formic acid, glutamic acid, methanesulfonic acid, ethanesulfonic acid, benzenesulfonic acid, lactic acid, oxalic acid, para-bromophenylsulfonic acid, carbonic acid, succinic acid, citric acid, benzoic acid and acetic acid, as well as related inorganic and organic acids. Such pharmaceutically acceptable salts thus include sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephthalate, sulfonate, xylene sulfonate, phenylacetate, phenylpropionate, phenylbutyrate, citrate, lactate, 3-hydroxybutyrate, glycolate, maleate, tartrate, methanesulfonate, propanesulfonate, naphthalene-1-sulfonate, naphthalene-2-sulfonate, mandelate and other salts. In one embodiment, pharmaceutically acceptable acid addition salts include those formed with mineral acids such as hydrochloric acid and hydrobromic acid, and especially those formed with organic acids such as maleic acid. In one embodiment, the acids commonly employed to form pharmaceutically acceptable salts include the above-listed inorganic acids, wherein at least one hydrogen is replaced with deuterium.

The term "stable compounds," as used herein, refers to compounds which possess stability sufficient to allow for their manufacture and which maintain the integrity of the compound for a sufficient period of time to be useful for the purposes detailed herein (e.g., formulation into therapeutic products, intermediates for use in production of therapeutic compounds, isolatable or storable intermediate compounds, treating a disease or condition responsive to therapeutic agents).

"D" and "d" both refer to deuterium. "Stereoisomer" refers to both enantiomers and diastereomers. "Tert" and "t-" each refer to tertiary. "US" refers to the United States of America.

"Substituted with deuterium" refers to the replacement of one or more hydrogen atoms with a corresponding number of deuterium atoms.

The term "prodrug moiety" includes moieties which can be metabolized in vivo to a hydroxyl group and moieties which may advantageously remain esterified in vivo. Preferably, the prodrugs moieties are metabolized in vivo by esterases or by other mechanisms to hydroxyl groups or other advantageous groups. Examples of prodrugs and their uses are well known in the art (See, e.g., Berge et al. (1977) "Pharmaceutical Salts", *J. Pharm. Sci.* 66:1-19).

"The term "alkyl" refers to a monovalent saturated hydrocarbon group. $C_1$-$C_6$ alkyl is an alkyl having from 1 to 6 carbon atoms. An alkyl may be linear or branched. Examples of alkyl groups include methyl; ethyl; propyl, including n-propyl and isopropyl; butyl, including n-butyl, isobutyl, sec-butyl, and t-butyl; pentyl, including, for example, n-pentyl, isopentyl, and neopentyl; and hexyl, including, for example, n-hexyl and 2-methylpentyl.

The term "alkenyl" refers to a monovalent unsaturated hydrocarbon group where the unsaturation is represented by a double bond. $C_2$-$C_6$ alkenyl is an alkenyl having from 2 to 6 carbon atoms. An alkenyl may be linear or branched. Examples of alkenyl groups include $CH_2=CH-$, $CH_2=C(CH_3)-$, $CH_2=CH-CH_2-$, $CH_3-CH=CH-CH_2-$, $CH_3-CH=C(CH_3)-$ and $CH_3-CH=CH-CH(CH_3)-CH_2-$. Where double bond stereoisomerism is possible, the stereochemistry of an alkenyl may be (E), (Z), or a mixture thereof.

The term "haloalkyl" includes mono, poly, and perhaloalkyl groups where the halogens are independently selected from fluorine, chlorine, bromine, and iodine.

"Alkoxy" means an alkyl radical attached through an oxygen linking atom, represented by —O-alkyl. For example, "$(C_1$-$C_4)$alkoxy" includes methoxy, ethoxy, propoxy, and butoxy.

The term "aryl" used alone or as part of a larger moiety as in "aralkyl", "aralkoxy", or "aryloxyalkyl", refers to an aromatic carbocyclic ring system having, unless otherwise specified, a total of 6 to 14 ring members. The term "aryl" may be used interchangeably with the term "aryl ring", "aryl group", "aryl moiety," or "aryl radical". In certain embodiments of the present disclosure, "aryl" refers to an aromatic ring system which includes, but is not limited to, phenyl (abbreviated as "Ph"), naphthyl and the like. It will be understood that when specified, optional substituents on an aryl group (e.g., in the case of an optionally substituted aryl or aryl which is optionally substituted) may be present on any substitutable position, i.e., any ring carbon substituted with hydrogen.

The term "carbocyclyl" (also referred to herein as "carbocycle" or "cycloaliphatic", as used herein, means a monocyclic, bicyclic (e.g., a bridged or spiro bicyclic ring), polycyclic (e.g., tricyclic), or fused hydrocarbon ring system that is completely saturated or that contains one or more units of unsaturation, but where there is no aromatic ring. Cycloalkyl is a completely saturated carbocycle. Monocyclic carbocyclyl groups include, without limitation, cyclopropyl, cyclobutyl, cyclopentyl, cyclopentenyl, cyclohexyl, cyclohexenyl, cycloheptyl, cycloheptenyl, and cyclooctyl. Bridged bicyclic carbocyclyl groups include, without limitation, bicyclo[3.2.1]octane, bicyclo[2.2.1]heptane, bicyclo[3.1.0]hexane, and the like. Spiro bicyclic carbocyclyl groups include, e.g., spiro[3.6]decane, spiro[4.5]decane, and the like. Fused carbocyclyl rings include, e.g., decahydronaphthalene, octahydropentalene, and the like. It will be understood that when specified, optional substituents on a carbocyclyl (e.g., in the case of an optionally substituted carbocyclyl or carbocyclyl which is optionally substituted) may be present on any substitutable position and, include, e.g., the position at which the carbocyclyl group is attached.

The term "heteroaryl" used alone or as part of a larger moiety as in "heteroarylalkyl", "heteroarylalkoxy", or "heteroarylaminoalkyl", refers to a 5-10-membered aromatic radical containing 1-4 heteroatoms selected from N, quaternary ammonium cation, O, and S, and includes, for example, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The term "heteroaryl" may be used interchangeably with the terms "heteroaryl ring", "heteroaryl group", or "heteroaromatic". The terms "heteroaryl" and "heteroar-", as used herein, also include groups in which a heteroaromatic ring is fused to one or more aryl rings, where the radical or point of attachment is on the heteroaromatic ring. Nonlimiting examples include indolyl, indazolyl, benzimidazolyl, benzthiazolyl, quinolyl, quinazolinyl, and quinoxalinyl. It will be understood that when specified, optional substituents on a heteroaryl group may be present on any substitutable position (carbon and nitrogen).

The term "heterocyclyl" means a 3-12 membered (e.g., a 4-, 5-, 6- and 7-membered) saturated or partially unsaturated heterocyclic ring containing 1 to 4 heteroatoms independently selected from N, O, and S. It can be monocyclic, bicyclic (e.g., a bridged, fused, or spiro bicyclic ring), or tricyclic. The terms "heterocycle", "heterocyclyl", "heterocyclyl ring", "heterocyclic group", "heterocyclic moiety", and "heterocyclic radical", are used interchangeably herein. A heterocyclyl ring can be attached to its pendant group at any heteroatom or carbon atom that results in a stable structure. Examples of such saturated or partially unsaturated heterocyclic radicals include, without limitation, tetrahydrofuranyl, tetrahydrothienyl, terahydropyranyl, pyrrolidinyl, pyridinonyl, pyrrolidonyl, piperidinyl, oxazolidinyl, piperazinyl, dioxanyl, dioxolanyl, morpholinyl, dihydrofuranyl, dihydropyranyl, dihydropyridinyl, tetrahydropyridinyl, dihydropyrimidinyl, 1-azaspiro[4.5]decane, and tetrahydropyrimidinyl. A heterocyclyl group may be mono- or bicyclic. The term "heterocyclyl" also includes, e.g., unsaturated heterocyclic radicals fused to another unsaturated heterocyclic radical or aryl or heteroaryl ring, such as for example, tetrahydronaphthyridine, indolinone, dihydropyrrolotriazole, imidazopyrimidine, quinolinone, dioxaspirodecane. It will also be understood that when specified, optional substituents on a heterocyclyl group may be present on any substitutable position and, include, e.g., the position at which the heterocyclyl is attached (e.g., in the case of an optionally substituted heterocyclyl or heterocyclyl which is optionally substituted).

The term "spiro" refers to rings that shares one ring atom (e.g., carbon).

The term "fused" refers to rings that share two adjacent ring ring atoms with one another.

The term "bridged" refers to rings that share at least three ring atoms with one another.

As described herein, compounds herein may contain "optionally substituted" moieties. Unless otherwise indicated, an "optionally substituted" group may have a suitable substituent that results in the formation of stable or chemically feasible compounds. Examples include halogen, =O, —CN, —OR$^c$, —NR$^a$R$^b$, —S(O)$_i$R$^c$, —NR$^d$S(O)$_2$R$^c$, —S(O)$_2$NR$^e$R$^f$, —C(=O)OR$^c$, —OC(=O)R$^c$, —OC(=O)R$^c$, —OC(=S)OR$^c$, —C(=S)OR$^c$, —O(C=S)R$^c$, —C(=O)NR$^e$R$^f$, —NR$^d$C(=O)R$^c$, —C(=S)NR$^e$R$^f$, —NR$^d$C(=S)R$^c$, —NR$^d$(C=O)OR$^c$, —O(C=O)NR$^e$R$^f$, —NR$^d$(C=S)OR$^c$, —O(C=S)NR$^e$R$^f$, —NR$^d$(C=O)NR$^e$R$^f$, —NR$^d$(C=S)NR$^e$R$^f$, —C(=S)R$^c$, —C(=O)R$^c$, —(C$_1$-C$_6$)alkyl, cycloalkyl, —(CH$_2$)$_{1-4}$-cycloalkyl, heterocyclyl, —(CH$_2$)$_{1-4}$-heterocyclyl, aryl, —(CH$_2$)$_{1-4}$-aryl, heteroaryl and —(CH$_2$)$_{1-4}$-heteroaryl, wherein each of the (C$_1$-C$_6$)alkyl, cycloalkyl, —(CH$_2$)$_{1-4}$-cycloalkyl, heterocyclyl, —(CH$_2$)$_{1-4}$-heterocyclyl, aryl, —(CH$_2$)$_{1-4}$-aryl, heteroaryl and —(CH$_2$)$_{1-4}$-heteroaryl are optionally substituted with halogen, —OR$^c$, —NO$_2$, —CN, —NR$^d$C(=O)R$^c$, —NR$^g$R$^h$, —S(O)$_i$R$^c$, —C(=O)OR$^c$, —C(=O)NR$^e$R$^f$, —C(=O)R$^c$, (C$_1$-C$_3$)alkyl, halo(C$_1$-C$_3$)alkyl, (C$_1$-C$_3$)alkoxy(C$_1$-C$_3$)alkyl, (C$_1$-C$_3$)alkoxy, and halo(C$_1$-C$_3$)alkoxy; wherein R$^a$ and R$^b$ are each independently selected from hydrogen and (C$_1$-C$_6$)alkyl optionally substituted with 1 to 3 substituents independently selected from halogen, hydroxy, —COOH, —NR$^g$R$^h$, and —(C$_1$-C$_3$)alkoxy; R$^c$ is hydrogen or (C$_1$-C$_6$)alkyl optionally substituted with 1 to 3 substituents independently selected from halogen, —NR$^g$R$^h$, hydroxyl, and (C$_1$-C$_3$)alkoxy; R$^d$ is hydrogen or (C$_1$-C$_6$)alkyl optionally substituted with 1 to 3 substituents independently selected from halogen, —NR$^g$R$^h$, hydroxyl, and (C$_1$-C$_3$)alkoxy; R$^e$ and R$^f$ are each independently selected from hydrogen and (C$_1$-C$_6$)alkyl optionally substituted with 1 to 3 substituents independently selected from halogen, —NR$^g$R$^h$, hydroxyl, and (C$_1$-C$_3$)alkoxy; or R$^e$ and R$^f$, together with the nitrogen to which they are attached, form a 3-8 membered ring optionally substituted with 1 to 3 substituents independently selected from halogen, —NR$^g$R$^h$, —CN, (C$_1$-C$_6$)alkyl, halo(C$_1$-C$_6$)alkyl, (C$_1$-C$_3$)alkoxy, halo(C$_1$-C$_3$)alkoxy, and (C$_1$-C$_3$)alkoxy(C$_1$-C$_6$)alkyl; R$^g$ and R$^h$ are each independently selected from hydrogen, (C$_1$-C$_6$)alkyl, halo(C$_1$-C$_6$)alkyl, hydroxy(C$_1$-C$_6$)alkyl, and (C$_1$-C$_3$)alkoxy(C$_1$-C$_6$)alkyl; and i is 0, 1 or 2.

Throughout this specification, a variable may be referred to generally (e.g., "each R") or may be referred to specifically (e.g., R$^1$, R$^2$, R$^3$, etc.). Unless otherwise indicated, when a variable is referred to generally, it is meant to include all specific embodiments of that particular variable.

Therapeutic Compounds

The present invention provides a compound of Formula I:

(I)

or a pharmaceutically acceptable salt thereof, wherein:
each of X$^1$, X$^2$, X$^3$, X$^4$, X$^5$, X$^6$, and X$^7$ is independently hydrogen or deuterium;

R$^1$ is selected from deuterium, hydrogen, fluoro, —CF$_3$, —CH$_3$, —CH$_2$D, —CHD$_2$ and —CD$_3$; and R$^2$ is selected from hydrogen, and a prodrug moiety.

In some embodiments, X$^1$, X$^2$, X$^3$, and X$^4$ are the same. In one aspect of these embodiments, X$^1$, X$^2$, X$^3$, and X$^4$ are all hydrogen. In an alternate aspect of these embodiments, X$^1$, X$^2$, X$^3$, and X$^4$ are all deuterium.

In some embodiments, X$^6$ and X$^7$ are the same. In one aspect of these embodiments, X$^6$ and X$^7$ are hydrogen. In an alternate aspect of these embodiments, X$^6$ and X$^7$ are deuterium.

In some embodiments, X$^5$ is deuterium.

In some embodiments, X$^5$ is hydrogen.

In some embodiments, X$^1$, X$^2$, X$^3$, X$^4$, X$^5$, X$^6$ and X$^7$ are all the same. In one aspect of these embodiments, X$^1$, X$^2$, X$^3$, X$^4$, X$^5$, X$^6$ and X$^7$ are all hydrogen. In one aspect of these embodiments, X$^1$, X$^2$, X$^3$, X$^4$, X$^5$, X$^6$ and X$^7$ are all deuterium.

In some embodiments, R$^1$ is selected from deuterium, hydrogen, fluoro, —CF$_3$, —CH$_3$, and —CD$_3$. In one aspect of these embodiments, R$^1$ is selected from hydrogen, deuterium, fluoro and —CF$_3$. In a more specific aspect of these embodiments, R$^1$ is selected from hydrogen, fluoro and —CF$_3$. In an even more specific aspect of these embodiments, R$^1$ is hydrogen.

In some embodiments, R$^2$ is hydrogen.

In alternate embodiments, R$^2$ is a prodrug moiety. In one aspect of these embodiments, R$^2$ is a prodrug moiety described in WO2007075901 (see the definition of R$^{xy}$ therein) and WO2003090691. In a more specific aspect of these embodiments, R$^2$ is a prodrug moiety selected from:

—[C(R$^3$)(R$^3$)—O]$_{0-1}$—P(=O)(OM)$_2$;

—[C(R$^3$)(R$^3$)—O]$_{0-1}$—P(=O)(O)(OM');

—[C(R$^3$)(R$^3$)—O]$_{0-1}$—C(=O)—R$^4$; and

—C(R$^3$)(R$^3$)—O—R$^4$, wherein:

each R$^3$ is independently selected from hydrogen, C$_1$-C$_4$ alkyl and C$_1$-C$_4$ haloalkyl;

each M is independently selected from hydrogen, Li, Na, K, optionally substituted C$_1$-C$_4$ alkyl, and optionally substituted C$_2$-C$_4$ alkenyl;

each M' is independently selected from Mg, Ca, Ba, optionally substituted C$_1$-C$_4$ alkyl, and optionally substituted C$_2$-C$_4$ alkenyl; and R$^4$ is optionally substituted C$_1$-C$_4$ alkyl.

In an even more specific embodiment, R$^2$ is selected from —CH$_2$—O—C(O)—CH$_3$, —CH$_2$—O—C(O)—C(CH$_3$)$_3$, —CH$_2$—O—CH(CH$_3$)$_2$, and —C(O)CH$_3$. In another more specific embodiment, R$^2$ is selected from —P(=O)(OM)$_2$, —P(=O)(O)OM', —CH$_2$—P(=O)(OM)$_2$ and —CH$_2$—P(=O)(O)OM', wherein M is a metal cation selected from Li$^+$, Na$^+$, and K+; and M' is a metal cation selected from Mg$^{2+}$, Ca$^{2+}$, and Ba$^{2+}$.

In another set of embodiments, any atom not designated as deuterium in any of the embodiments, examples or aspects set forth above is present at its natural isotopic abundance.

In one embodiment, each of X$^1$, X$^2$, X$^3$, and X$^4$ are the same; X$^6$ and X$^7$ are the same; R$^2$ is hydrogen; and the compound of Formula I is any one of the compounds set forth below in Table 1.

TABLE 1

Exemplary compounds of the invention.

| Cmpd # | $X^1$-$X^4$ | $X^6$-$X^7$ | $X^5$ | $R^1$ |
|---|---|---|---|---|
| 100 | H | H | H | H |
| 101 | H | H | D | H |
| 102 | D | D | H | H |
| 103 | D | D | D | H |
| 104 | H | H | H | D |
| 105 | H | H | D | D |
| 106 | D | D | H | D |
| 107 | D | D | D | D |
| 108 | H | H | H | $CH_3$ |
| 109 | H | H | D | $CH_3$ |
| 110 | D | D | H | $CH_3$ |
| 111 | D | D | D | $CH_3$ |
| 112 | H | H | H | $CD_3$ |
| 113 | H | H | D | $CD_3$ |
| 114 | D | D | H | $CD_3$ |
| 115 | D | D | D | $CD_3$ |
| 116 | H | H | H | F |
| 117 | H | H | D | F |
| 118 | D | D | H | F |
| 119 | D | D | D | F |
| 120 | H | H | H | $CF_3$ |
| 121 | H | H | D | $CF_3$ |
| 122 | D | D | H | $CF_3$ |
| 123 | D | D | D | $CF_3$ |
| 124 | H | D | H | H |
| 125 | H | D | D | H |
| 126 | D | H | H | H |
| 127 | D | H | D | H |
| 128 | H | D | H | D |
| 129 | H | D | D | D |
| 130 | D | H | H | D |
| 131 | D | H | D | D |
| 132 | H | D | H | $CH_3$ |
| 133 | H | D | D | $CH_3$ |
| 134 | D | H | H | $CH_3$ |
| 135 | D | H | D | $CH_3$ |
| 136 | H | D | H | $CD_3$ |
| 137 | H | D | D | $CD_3$ |
| 138 | D | H | H | $CD_3$ |
| 139 | D | H | D | $CD_3$ |
| 140 | H | D | H | F |
| 141 | H | D | D | F |
| 142 | D | H | H | F |
| 143 | D | H | D | F |
| 144 | H | D | H | $CF_3$ |
| 145 | H | D | D | $CF_3$ |
| 146 | D | H | H | $CF_3$ |
| 147 | D | H | D | $CF_3$ | or a pharmaceutically acceptable salt thereof, wherein any atom not designated as deuterium is present at its natural isotopic abundance.

In some embodiments of a compound of this invention, when $X^1$, $X^2$, $X^3$, $X^4$, $X^5$, $X^6$, or $X^7$ is deuterium, the level of deuterium incorporation at each X designated as deuterium is at least 52.5%, at least 75%, at least 82.5%, at least 90%, at least 95%, is at least 97%, or at least 99%.

In some embodiments of a compound of this invention, when $R^1$ comprises deuterium, the level of deuterium incorporation at each designated deuterium is at least 52.5%, at least 75%, at least 82.5%, at least 90%, at least 95%, is at least 97%, or at least 99%.

Such methods can be carried out utilizing corresponding deuterated and optionally, other isotope-containing reagents and/or intermediates to synthesize the compounds delineated herein, or invoking standard synthetic protocols known in the art for introducing isotopic atoms to a chemical structure.

Exemplary Synthesis

The synthesis of compounds of Formula I may be readily achieved by synthetic chemists of ordinary skill by reference to the Exemplary Synthesis. Relevant procedures analogous to those of use for the preparation of compounds of Formula I, and intermediates thereof are disclosed using well known methods in the art disclosed, for instance in U.S. Pat. No. 8,354,427 and Hadida, S. et al., Journal of Medicinal Chemistry, 57(23), 9776-9795; 2014. Such methods can be carried out utilizing corresponding deuterated and optionally, other isotope-containing reagents and/or intermediates to synthesize the compounds delineated herein, or invoking standard synthetic protocols known in the art for introducing isotopic atoms to a chemical structure.

A convenient method for synthesizing compounds of Formula I is depicted in Scheme 1 below.

Scheme 1: General Synthesis of Compounds of Formula I

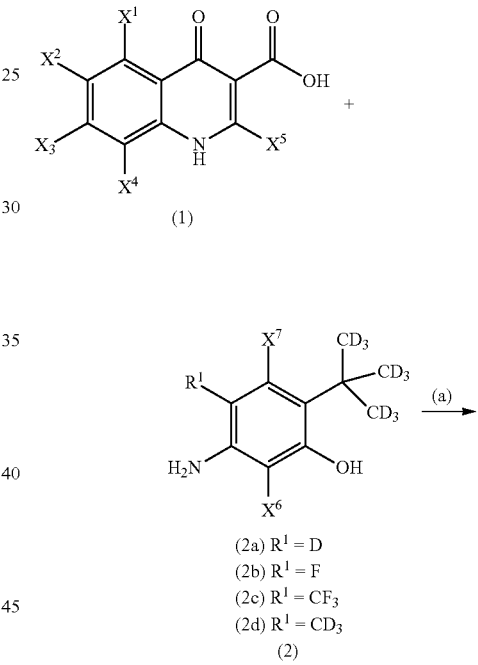

(1)

(2a) $R^1 = D$
(2b) $R^1 = F$
(2c) $R^1 = CF_3$
(2d) $R^1 = CD_3$
(2)

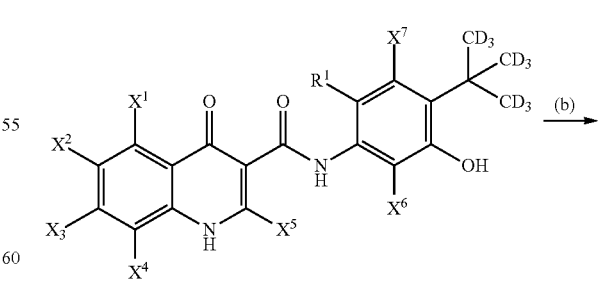

Formula I
(Ia) $R^1 = D$
(Ib) $R^1 = F$
(Ic) $R^1 = CF_3$
(Id) $R^1 = CD_3$

-continued

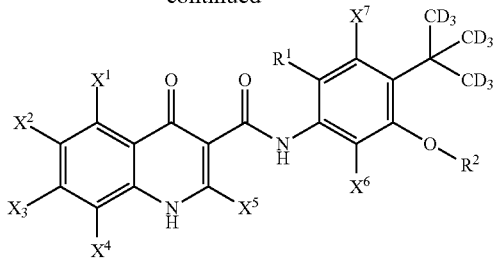

Formula I; $R^2$ = prodrug moiety
(Ia) $R^1$ = D
(Ib) $R^1$ = F
(Ic) $R^1$ = $CF_3$
(Id) $R^1$ = $CD_3$ Reagents and conditions: (a) HBTU, $Et_3N$; (b) when $R^2$ = ester moiety: EDC, DMAP; or when $R^2$ = ether moiety: e.g. $ClCH_2CO_2CH_3$, $K_2CO_3$, KI; or when $R^2$ = phosphate moiety: (i) $(iPr)_2N$—$P(OBn)_2$, tetrazole, t-BuOOH; (ii) $H_2$, Pd, $M(OH)_n$ e.g. NaOH, $H_2O$; or for e.g. when $R^2$ = $CH_2OP(O)OH_2$: (i) NaH, dibenzyl phosphonyl methyltriflate; (ii) 4M HCl/Dioxane.

In a manner analogous to a procedure described in U.S. Pat. No. 8,354,427, appropriately deuterated quinoline carboxylic acid intermediate (1) is coupled with appropriately deuterated aniline intermediate (2) using amide coupling reagent such as HBTU in the presence of triethylamine to produce appropriately deuterated amide compounds of Formula I. Furthermore, by analogy to a procedure described in WO 200707590, or described in WO 2003090691, or described by Wei, T. et al., Synthetic Communications, 35(13), 1759-1764; 2005, or described by Ibrahimi, O., et al., Bioorganic & Medicinal Chemistry Letters, 10(5), 457-460; 2000, appropriately deuterated compounds of Formula I, wherein $R^2$=H is subsequently treated with reagents bearing desired $R^2$ moieties using appropriate reaction conditions, to produce prodrugs of appropriately deuterated compounds of Formula I.

Using commercially available reagents and deuterated reagents that can be readily prepared by known methods, compounds of Formula I can be prepared with greater than 90% or greater than 95% deuterium incorporation at each position designated as D (see below for details).

Appropriately deuterated starting material (1), for use in the preparation of compounds of Formula I according to Scheme 1 may be prepared from corresponding deuterated reagents as exemplified below.

Intermediate (1)

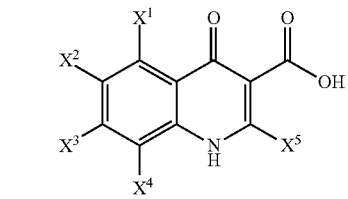

(1a): $X^1$ = $X^2$ = $X^3$ = $X^4$ = $X^5$ = D
(1b): $X^1$ = $X^2$ = $X^3$ = $X^4$ = D; $X^5$ = H
(1c): $X^1$ = $X^2$ = $X^3$ = $X^4$ = H; $X^5$ = D

Appropriately deuterated intermediates (1a, 1b, and 1c) are prepared according to methods described in U.S. Pat. No. 8,865,902. Use of appropriately deuterated reagents allows deuterium incorporation at the $X^1$, $X^2$, $X^3$, $X^4$ and $X^5$ positions of a compound of Formula I, or any appropriate intermediate herein, e.g., 90, 95, 97, or 99% deuterium incorporation at any of $X^1$, $X^2$, $X^3$, $X^4$, and/or $X^5$.

Using commercially available reagents and deuterated reagents that can be readily prepared by known methods, compounds of Formula I can be prepared with greater than 90% or greater than 95% deuterium incorporation at each position designated as D (see below for details).

Appropriately deuterated intermediate (2a), for use in the preparation of compounds of Formula I according to Scheme 1 may be prepared from corresponding deuterated reagents exemplified in Scheme 2a below.

Scheme 2a: Preparation of Intermediate (2a)($R^1$ = D)

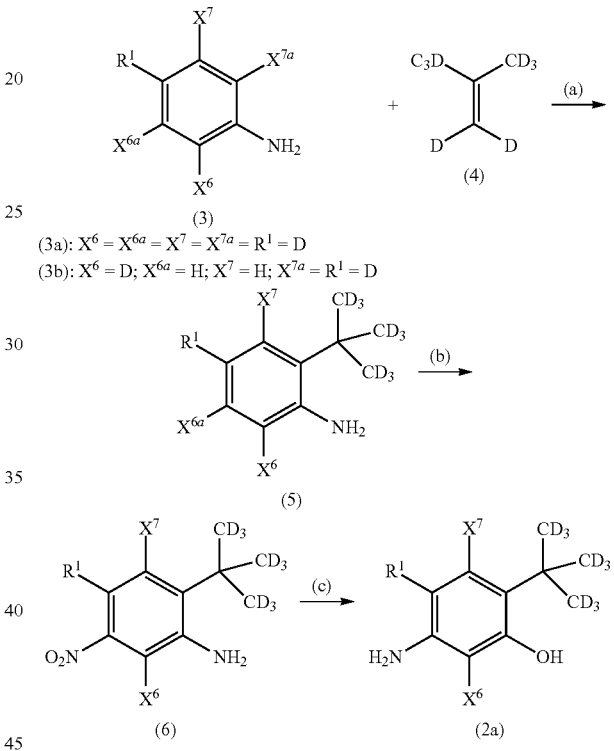

(3a): $X^6$ = $X^{6a}$ = $X^7$ = $X^{7a}$ = $R^1$ = D
(3b): $X^6$ = D; $X^{6a}$ = H; $X^7$ = H; $X^{7a}$ = $R^1$ = D

Reagents and conditions: (a) $Al_2O_3$, $SiO_2$; (b) $KNO_3$, $H_2SO_4$; (c) (i) $NaNO_2$, $H_2SO_4$, $H_2O$; (ii) $NH_4CO_2H$, Pd—C.

In a manner analogous to a procedure described in EP 336134 A2, appropriately deuterated aniline intermediate (3) is treated with appropriately deuterated propene intermediate (4) in the presence of silica-alumina catalyst system to furnish appropriately deuterated tert-butyl aniline intermediate (5). Subsequent nitration of intermediate (5) with potassium nitrate in the presence of an acid such as, sulfuric acid at low temperature produces appropriate deuterated nitro aniline intermediate (6) by analogy to a procedure described in WO2010022055 or WO 2006002421. Diazotization followed by quenching with water and reduction of the nitro moiety using ammonium formate catalytic transfer hydrogenation condition produces appropriately deuterated aniline intermediate (2a) by analogy to a procedure described in U.S. Pat. No. 8,354,427.

The following intermediates (3) are commercially available: Aniline-$d_7$ (98 atom % D) (3a), benzen-2,4,6-$d_3$-amine (90-95 atom % D) (3b) or prepared according to a procedure described by Martins, A. et al., Organic Letters, 10(19), 4351-4353; 2008. 2-Methylpropene-d$_8$ (99 atom % D) intermediate (4) is commercially available.

Use of appropriately deuterated reagents allows deuterium incorporation at the X$^6$, X$^7$ and/or R$^1$ positions of a compound of Formula I, or any appropriate intermediate herein, e.g., 90, 95, 97, or 99% deuterium incorporation at any X$^6$, X$^7$ and/or R$^1$.

Using commercially available reagents and deuterated reagents that can be readily prepared by known methods, compounds of Formula I can be prepared with greater than 90% or greater than 95% deuterium incorporation at each position designated as D (see below for details).

Appropriately deuterated intermediate (2b), for use in the preparation of compounds of Formula I according to Scheme 1 may be prepared from corresponding deuterated reagents exemplified in Scheme 2b below.

Scheme 2b: Preparation of Intermediate (2b) (R$^1$ = F)

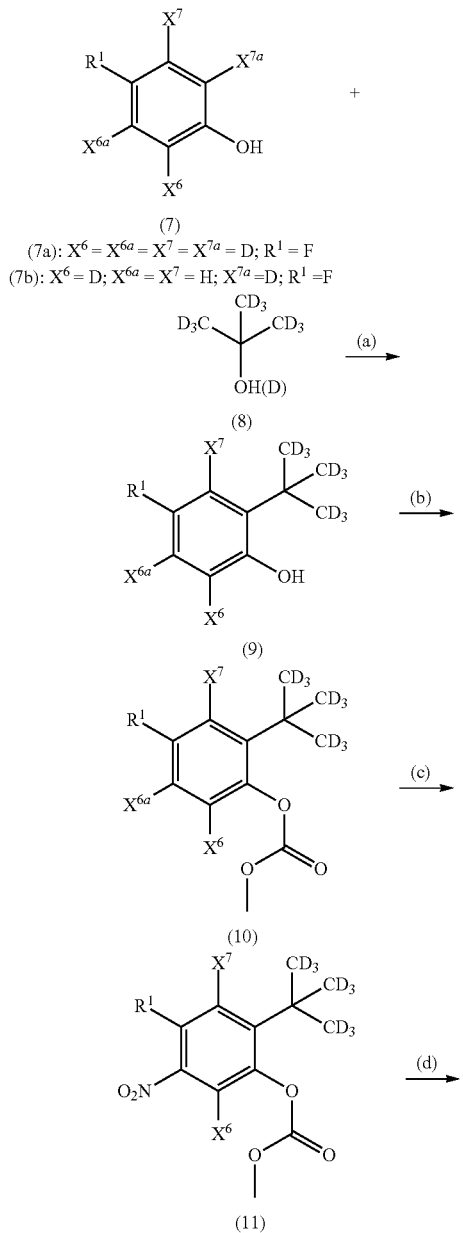

(7)
(7a): X$^6$ = X$^{6a}$ = X$^7$ = X$^{7a}$ = D; R$^1$ = F
(7b): X$^6$ = D; X$^{6a}$ = X$^7$ = H; X$^{7a}$ = D; R$^1$ = F

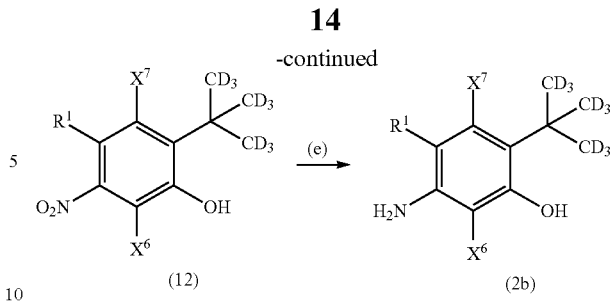

Reagents and conditions: (a) D$_2$SO$_4$; (b) CH$_3$CO$_2$Cl, Et$_3$N; (c) HNO$_3$, H$_2$SO$_4$; (d) Piperidine; (e) NH$_4$CO$_2$H, Pd/C.

In a manner analogous to a procedure described by Hadida, S. et al., Journal of Medicinal Chemistry, 57(23), 9776-9795; 2014, Friedel-Crafts alkylation of appropriately deuterated fluorophenol intermediate (7) with appropriately deuterated tert-butanol intermediate (8) affords appropriately deuterated phenol intermediate (9) which is protected with methyl chloroformate in the presence of a base such as triethylamine producing appropriately deuterated carbonate intermediate (10). Subsequent nitration affords appropriately deuterated nitrobenzene intermediate (11), which is treated with piperidine to remove the protecting group, furnishing appropriately deuterated nitrophenol intermediate (12). Finally, nitro reduction under catalytic transfer hydrogenation produces appropriately deuterated aniline intermediate (2b).

The following intermediate (7) is commercially available: 4-Fluorophenol-d$_5$ (98 atom % D) (7a), and 4-fluoro-phen-2,6-d$_2$-ol (7b) is prepared in accordance with a procedure described by Perrin, C., et al., Journal of the American Chemical Society, 129(14), 4490-4497; 2007.

The following intermediates (8) are commercially available: tert-butan-d$_9$-ol (98 atom % D) or tert-butanol-d$_{10}$ (99 atom % D) (8a), tert-butyl-1,1,1,3,3,3-d$_6$ alcohol (99 atom % D) (8b), and tert-butyl-1,1,1-d$_3$ alcohol (99 atom % D) (8c). Use of appropriately deuterated reagents allows deuterium incorporation at the X$^6$, X$^7$ and/or R positions of a compound of Formula I, or any appropriate intermediate herein, e.g., 90, 95, 97, or 99% deuterium incorporation at any X$^6$, X$^7$ and/or R$^1$.

Using commercially available reagents and deuterated reagents that can be readily prepared by known methods, compounds of Formula I can be prepared with greater than 90% or greater than 95% deuterium incorporation at each position designated as D (see below for details).

Appropriately deuterated intermediate (2c), for use in the preparation of compounds of Formula I according to Scheme 1 may be prepared from corresponding deuterated reagents exemplified in Scheme 2c below.

Scheme 2c: Preparation of Intermediate (2c)(R$^1$ = CF$_3$)

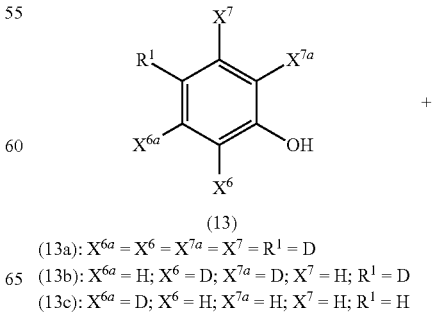

(13)
(13a): X$^{6a}$ = X$^6$ = X$^{7a}$ = X$^7$ = R$^1$ = D
(13b): X$^{6a}$ = H; X$^6$ = D; X$^{7a}$ = D; X$^7$ = H; R$^1$ = D
(13c): X$^{6a}$ = D; X$^6$ = H; X$^{7a}$ = H; X$^7$ = H; R$^1$ = H

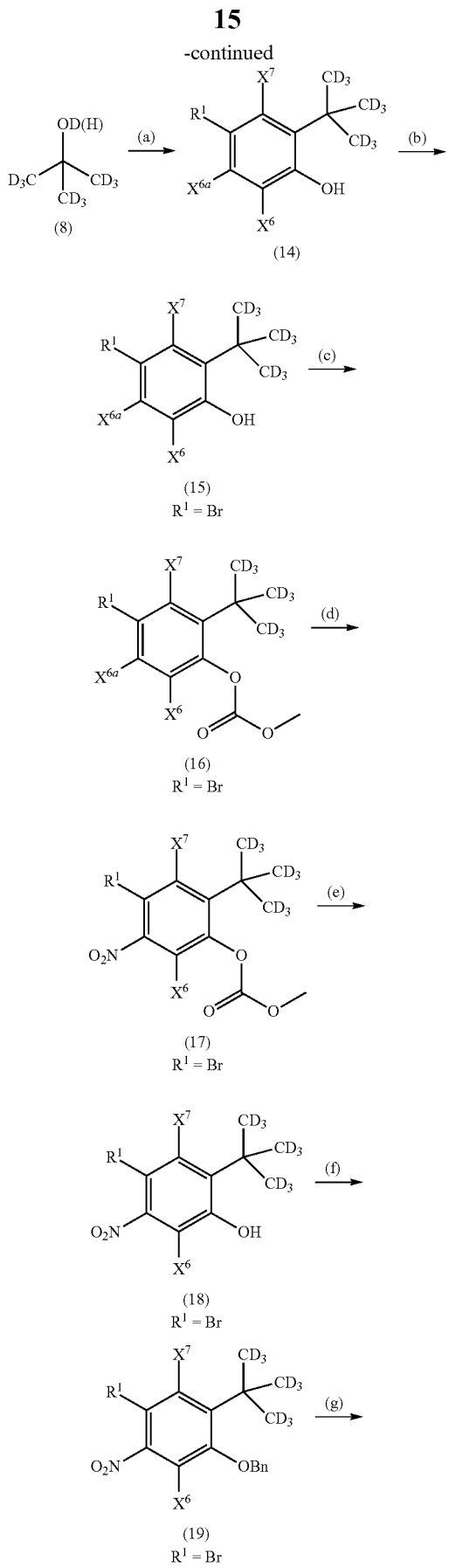
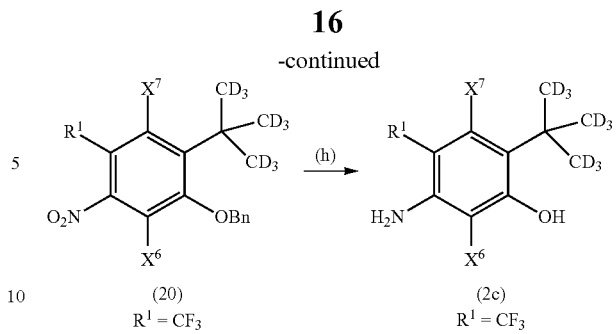

Reagents and conditions: (a) H₂SO₄; (b) NBS; (c) methyl chloroformate, Et₃N; (d) KNO₃, H₂SO₄; (e) KOH; (f) BnBr, Cs₂CO₃; (g) ClCF₂CO₂CH₃, KF, KBr, CuI; (h) HCO₂NH₄, Pd/C.

In a manner analogous to a procedure described U.S. Pat. No. 8,354,427 B2, appropriately deuterated phenol intermediate (13) is treated with appropriately deuterated tert-butanol intermediate (8) providing appropriately deuterated butylated phenol intermediate (14). Selective bromination with a source of bromine such as NBS affords appropriately deuterated bromophenol intermediate (15), followed by protection of the phenol moiety with methyl chloroformate in the presence of a base such as triethylamine to produce appropriately deuterated carbonate intermediate (16). Subsequent nitration affords appropriately deuterated nitro intermediate (17), which is treated with a base such as KOH to remove the protecting group, furnishing appropriately deuterated nitrophenol intermediate (18). Further benzyl protection of phenol moiety produces appropriately deuterated and protected nitrophenol intermediate (19) and subsequent treatment of bromo moiety of intermediate (19) with methyl chlorodifluoroacetate in the presence of KF and catalytic amounts of CuI at elevated temperature produces corresponding and appropriately deuterated trifluoromethylated intermediate (20). Finally, nitro reduction under catalytic transfer hydrogenation produces appropriately deuterated aniline intermediate (2c).

The following intermediates (13) are commercially available: phenol-2,3,4,5,6-$d_5$ (98 atom % D) (13a), phenol-2,4,6-$d_3$ (98 atom % D) (13b), phenol-3,5-$d_2$ (97 atom % D) (13c). As previously described, the following intermediates (8) are commercially available: tert-butan-$d_9$-ol (98 atom % D) or tert-butanol-$d_{10}$ (99 atom % D) (8a), tert-butyl-1,1,1,3,3,3-$d_6$ alcohol (99 atom % D) (8b), and tert-butyl-1,1,1-$d_3$ alcohol (99 atom % D) (8c). Use of appropriately deuterated reagents allows deuterium incorporation at the $X^6$, $X^7$ and/or $R^1$ positions of a compound of Formula I, or any appropriate intermediate herein, e.g., 90, 95, 97, or 99% deuterium incorporation at any $X^6$, $X^7$ and/or $R^1$.

Using commercially available reagents and deuterated reagents that can be readily prepared by known methods, compounds of Formula I can be prepared with greater than 90% or greater than 95% deuterium incorporation at each position designated as D (see below for details).

Appropriately deuterated intermediate (2d), for use in the preparation of compounds of Formula I according to Scheme 1 may be prepared from corresponding deuterated reagents exemplified in Scheme 2d below.

Scheme 2d: Preparation of Intermediate (2d)

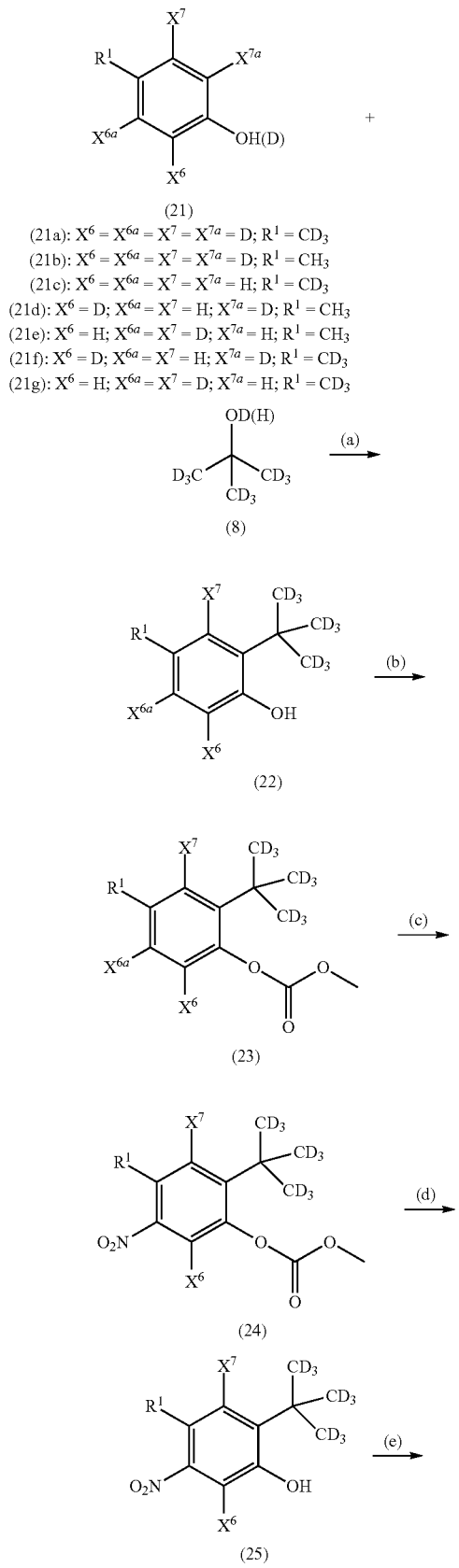

(21)
(21a): $X^6 = X^{6a} = X^7 = X^{7a} = D; R^1 = CD_3$
(21b): $X^6 = X^{6a} = X^7 = X^{7a} = D; R^1 = CH_3$
(21c): $X^6 = X^{6a} = X^7 = X^{7a} = H; R^1 = CD_3$
(21d): $X^6 = D; X^{6a} = X^7 = H; X^{7a} = D; R^1 = CH_3$
(21e): $X^6 = H; X^{6a} = X^7 = D; X^{7a} = H; R^1 = CH_3$
(21f): $X^6 = D; X^{6a} = X^7 = H; X^{7a} = D; R^1 = CD_3$
(21g): $X^6 = H; X^{6a} = X^7 = D; X^{7a} = H; R^1 = CD_3$

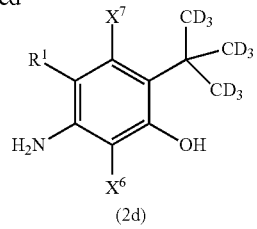

(2d)
(2da): $X^6 = X^7 = D; R^1 = CD_3$
(2db): $X^6 = X^7 = D; R^1 = CH_3$
(2dc): $X^6 = X^7 = H; R^1 = CD_3$
(2dd): $X^6 = X^7 = H; R^1 = CH_3$

Reagents and conditions: (a) Zr(O)Cl₂; (b) methyl chloroformate, Et₃N; (c) KNO₃, TMS-Cl, AlCl₃; (d) KOH; (e) H₂, Raney Nickel In a manner analogous to a procedure described by Yadav, et al., Synthetic Communications, 38(15), 2684-2691; 2008, zirconia mediated alkylation of appropriately deuterated cresol intermediate (21) with appropriately deuterated tert-butanol intermediate (8) at elevated temperature produces appropriately deuterated butyl intermediate (22). By analogy to a procedure described in U.S. Pat. No. 8,354,427, the phenol moiety of (22) is protected with methyl chloroformate in the presence of a base such as triethylamine furnishing appropriately deuterated carbonate intermediate (23) and subsequent nitration in the presence of TMS-Cl and AlCl₃ produces appropriately deuterated nitro intermediate (24). Treatment of (24) with a base such as KOH to remove the protecting group affords appropriately deuterated nitrophenol intermediate (25). Finally, nitro reduction with Raney nickel produces appropriately deuterated aniline intermediate (2d).

The following intermediates (21) are commercially available: p-Cresol-d₇ (98 atom % D) or p-Cresol-d₈ (21a), p-Cresol-2,3,5,6-d₄,OD (98 atom % D) (21b), p-Cresol-d₃ (methyl-d₃) (99 atom % D) (21c). Phen-2,6-d₂-ol, 4-methyl-(21d) is also commercially available or may be prepared according to Nakashima, Y. et al., Bulletin of the Chemical Society of Japan, 62(5), 1401-4; 1989. Phen-3,5-d₂-ol, 4-methyl-(21e) is prepared according to Fukui, Y. et al., Journal of the American Chemical Society, 136(44), 15607-15614; 2014. Intermediate (21f) may be prepared from (21c) by analogy to a procedure described by Nakashima, Y. et al., Bulletin of the Chemical Society of Japan, 62(5), 1401-4. Similarly, intermediate (21g) may be prepared from (21c) by analogy to a procedure described by Fukui, Y. et al., Journal of the American Chemical Society, 136(44), 15607-15614; 2014.

As previously described, the following intermediates (8) are commercially available: tert-butan-d₉-ol (98 atom % D) or tert-butanol-d₁₀ (99 atom % D) (8a), tert-butyl-1,1,1,3,3,3-d₆ alcohol (99 atom % D) (8b), and tert-butyl-1,1,1-d₃ alcohol (99 atom % D) (8c).

Use of appropriately deuterated reagents allows deuterium incorporation at the $X^6$, $X^7$ and/or $R^1$ positions of a compound of Formula I, or any appropriate intermediate herein, e.g., 90, 95, 97, or 99% deuterium incorporation at any $X^6$, $X^7$ and/or $R^1$.

The specific approaches and compounds shown above are not intended to be limiting. The chemical structures in the schemes herein depict variables that are hereby defined commensurately with chemical group definitions (moieties, atoms, etc.) of the corresponding position in the compound formulae herein, whether identified by the same variable name (i.e., $R^1$, $R^2$, $R^3$, etc.) or not. The suitability of a chemical group in a compound structure for use in the synthesis of another compound is within the knowledge of one of ordinary skill in the art.

Additional methods of synthesizing compounds of Formula I and their synthetic precursors, including those within routes not explicitly shown in schemes herein, are within the means of chemists of ordinary skill in the art. Synthetic chemistry transformations and protecting group methodologies (protection and deprotection) useful in synthesizing the applicable compounds are known in the art and include, for example, those described in Larock R, *Comprehensive Organic Transformations*, VCH Publishers (1989); Greene, T W et al., *Protective Groups in Organic Synthesis*, 3$^{rd}$ Ed., John Wiley and Sons (1999); Fieser, L et al., *Fieser and Fieser's Reagents for Organic Synthesis*, John Wiley and Sons (1994); and Paquette, L, ed., *Encyclopedia of Reagents for Organic Synthesis*, John Wiley and Sons (1995) and subsequent editions thereof.

Combinations of substituents and variables envisioned by this invention are only those that result in the formation of stable compounds.

Compositions

The invention also provides pharmaceutical compositions comprising an effective amount of a compound of Formula I (e.g., including any of the formulae herein), or a pharmaceutically acceptable salt of said compound; and a pharmaceutically acceptable carrier. The carrier(s) are "acceptable" in the sense of being compatible with the other ingredients of the formulation and, in the case of a pharmaceutically acceptable carrier, not deleterious to the recipient thereof in an amount used in the medicament.

Pharmaceutically acceptable carriers, adjuvants and vehicles that may be used in the pharmaceutical compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

If required, the solubility and bioavailability of the compounds of the present invention in pharmaceutical compositions may be enhanced by methods well-known in the art. One method includes the use of lipid excipients in the formulation. See "Oral Lipid-Based Formulations: Enhancing the Bioavailability of Poorly Water-Soluble Drugs (Drugs and the Pharmaceutical Sciences)," David J. Hauss, ed. Informa Healthcare, 2007; and "Role of Lipid Excipients in Modifying Oral and Parenteral Drug Delivery: Basic Principles and Biological Examples," Kishor M. Wasan, ed. Wiley-Interscience, 2006.

Another known method of enhancing bioavailability is the use of an amorphous form of a compound of this invention optionally formulated with a poloxamer, such as LUTROL and PLURONIC™ (BASF Corporation), or block copolymers of ethylene oxide and propylene oxide. See U.S. Pat. No. 7,014,866; and United States patent publications 20060094744 and 20060079502.

The pharmaceutical compositions of the invention include those suitable for oral, rectal, nasal, topical (including buccal and sublingual), vaginal or parenteral (including subcutaneous, intramuscular, intravenous and intradermal) administration. In certain embodiments, the compound of the formulae herein is administered transdermally (e.g., using a transdermal patch or iontophoretic techniques). Other formulations may conveniently be presented in unit dosage form, e.g., tablets, sustained release capsules, and in liposomes, and may be prepared by any methods well known in the art of pharmacy. See, for example, Remington: The Science and Practice of Pharmacy, Lippincott Williams & Wilkins, Baltimore, Md. (20th ed. 2000).

Such preparative methods include the step of bringing into association with the molecule to be administered ingredients such as the carrier that constitutes one or more accessory ingredients. In general, the compositions are prepared by uniformly and intimately bringing into association the active ingredients with liquid carriers, liposomes or finely divided solid carriers, or both, and then, if necessary, shaping the product.

In certain embodiments, the compound is administered orally. Compositions of the present invention suitable for oral administration may be presented as discrete units such as capsules, sachets, or tablets each containing a predetermined amount of the active ingredient; a powder or granules; a solution or a suspension in an aqueous liquid or a non-aqueous liquid; an oil-in-water liquid emulsion; a water-in-oil liquid emulsion; packed in liposomes; or as a bolus, etc. Soft gelatin capsules can be useful for containing such suspensions, which may beneficially increase the rate of compound absorption.

In the case of tablets for oral use, carriers that are commonly used include lactose and corn starch. Lubricating agents, such as magnesium stearate, are also typically added. For oral administration in a capsule form, useful diluents include lactose and dried cornstarch. When aqueous suspensions are administered orally, the active ingredient is combined with emulsifying and suspending agents. If desired, certain sweetening and/or flavoring and/or coloring agents may be added.

Compositions suitable for oral administration include lozenges comprising the ingredients in a flavored basis, usually sucrose and acacia or tragacanth; and pastilles comprising the active ingredient in an inert basis such as gelatin and glycerin, or sucrose and acacia.

Compositions suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampules and vials, and may be stored in a freeze dried (lyophilized) condition requiring only the addition of the sterile liquid carrier, for example water for injections, immediately prior to use. Extemporaneous injection solutions and suspensions may be prepared from sterile powders, granules and tablets.

Such injection solutions may be in the form, for example, of a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally-acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant.

The pharmaceutical compositions of this invention may be administered in the form of suppositories for rectal administration. These compositions can be prepared by mixing a compound of this invention with a suitable non-irritating excipient which is solid at room temperature but liquid at the rectal temperature and therefore will melt in the rectum to release the active components. Such materials include, but are not limited to, cocoa butter, beeswax and polyethylene glycols.

The pharmaceutical compositions of this invention may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art. See, e.g.: Rabinowitz J D and Zaffaroni A C, U.S. Pat. No. 6,803,031, assigned to Alexza Molecular Delivery Corporation.

Topical administration of the pharmaceutical compositions of this invention is especially useful when the desired treatment involves areas or organs readily accessible by topical application. For topical application topically to the skin, the pharmaceutical composition should be formulated with a suitable ointment containing the active components suspended or dissolved in a carrier. Carriers for topical administration of the compounds of this invention include, but are not limited to, mineral oil, liquid petroleum, white petroleum, propylene glycol, polyoxyethylene polyoxypropylene compound, emulsifying wax, and water. Alternatively, the pharmaceutical composition can be formulated with a suitable lotion or cream containing the active compound suspended or dissolved in a carrier. Suitable carriers include, but are not limited to, mineral oil, sorbitan monostearate, polysorbate 60, cetyl esters wax, cetearyl alcohol, 2-octyldodecanol, benzyl alcohol, and water. The pharmaceutical compositions of this invention may also be topically applied to the lower intestinal tract by rectal suppository formulation or in a suitable enema formulation. Topically-transdermal patches and iontophoretic administration are also included in this invention.

Application of the subject therapeutics may be local, so as to be administered at the site of interest. Various techniques can be used for providing the subject compositions at the site of interest, such as injection, use of catheters, trocars, projectiles, pluronic gel, stents, sustained drug release polymers or other device which provides for internal access.

In another embodiment, a composition of this invention further comprises a second therapeutic agent. The second therapeutic agent may be selected from any compound or therapeutic agent known to have or that demonstrates advantageous properties when administered with a compound having the same mechanism of action as VX-770.

Preferably, the second therapeutic agent is an agent useful in the treatment of a variety of conditions, including cystic fibrosis, Hereditary emphysema, Hereditary hemochromatosis, Coagulation-Fibrinolysis deficiencies, such as Protein C deficiency, Type 1 hereditary angioedema, Lipid processing deficiencies, such as Familial hypercholesterolemia, Type 1 chylomicronemia, Abetalipoproteinemia, Lysosomal storage diseases, such as I-cell disease/Pseudo-Hurler, Mucopolysaccharidoses, Sandhof/Tay-Sachs, Crigler-Najjar type II, Polyendocrinopathy/Hyperinsulemia, Diabetes mellitus, Laron dwarfism, Myleoperoxidase deficiency, Primary hypoparathyroidism, Melanoma, Glycanosis CDG type 1, Hereditary emphysema, Congenital hyperthyroidism, Osteogenesis imperfecta, Hereditary hypofibrinogenemia, ACT deficiency, Diabetes insipidus (DI), Neurophyseal DI, Neprogenic DI, Charcot-Marie Tooth syndrome, Perlizaeus-Merzbacher disease, neurodegenerative diseases such as Alzheimer's disease, Parkinson's disease, Amyotrophic lateral sclerosis, Progressive supranuclear palsy, Pick's disease, several polyglutamine neurological disorders asuch as Huntington, Spinocerebullar ataxia type I, Spinal and bulbar muscular atrophy, Dentatorubal pallidoluysian, and Myotonic dystrophy, as well as Spongiform encephalopathies, such as Hereditary Creutzfeldt-Jakob disease, Fabry disease, Straussler-Scheinker syndrome, chronic obstructive pulmonary disease (COPD), dry-eye disease, and Sjogren's disease.

In one embodiment, the second therapeutic agent is an agent useful in the treatment of cystic fibrosis.

In one embodiment, the second therapeutic agent is an agent useful in the treatment of COPD.

In one embodiment, the second therapeutic agent is an agent useful in the treatment of Parkinson's disease.

In one embodiment, the second therapeutic agent is an agent useful in the treatment of a bile duct disorder or a kidney ion channel disorder, including, but not limited to, Bartter's syndrome and Dent's disease.

In one embodiment, the second therapeutic agent is VX-809 (lumacaftor) or VX-661.

In another embodiment, the invention provides separate dosage forms of a compound of this invention and one or more of any of the above-described second therapeutic agents, wherein the compound and second therapeutic agent are associated with one another. The term "associated with one another" as used herein means that the separate dosage forms are packaged together or otherwise attached to one another such that it is readily apparent that the separate dosage forms are intended to be sold and administered together (within less than 24 hours of one another, consecutively or simultaneously).

In the pharmaceutical compositions of the invention, the compound of the present invention is present in an effective amount. As used herein, the term "effective amount" refers to an amount which, when administered in a proper dosing regimen, is sufficient to treat the target disorder.

The interrelationship of dosages for animals and humans (based on milligrams per meter squared of body surface) is described in Freireich et al., Cancer Chemother. Rep, 1966, 50: 219. Body surface area may be approximately determined from height and weight of the subject. See, e.g., Scientific Tables, Geigy Pharmaceuticals, Ardsley, N.Y., 1970, 537.

In one embodiment, an effective amount of a compound of this invention can range from about 0.02 to 2500 mg per treatment. In more specific embodiments the range is from about 0.2 to 1250 mg or from about 0.4 to 500 mg or most specifically from 2 to 250 mg per treatment. Treatment typically is administered one to two times daily. In one embodiment, the compound of the invention is administered two times daily in an amount between 50 and 300 mg each time. In one embodiment, the compound of the invention is administered once daily in an amount between 100 to 500 mg. In the foregoing embodiments, the compound is administered optionally in combination with a second agent. Examples of second agents include CFTR correctors, such as lumacaftor or VX-661. In some embodiments wherein the compound is administered optionally in combination with a second agent, the amount of compound is administered twice daily at between 100 mg and 300 mg each time, such as between 150 mg and 250 mg each time. In other embodiments wherein the compound is administered optionally in combination with a second agent, the amount of compound is administered three times daily at between 100 mg and 300 mg each time, such as between 150 mg and 250 mg each time.

Effective doses will also vary, as recognized by those skilled in the art, depending on the diseases treated, the severity of the disease, the route of administration, the sex, age and general health condition of the subject, excipient usage, the possibility of co-usage with other therapeutic treatments such as use of other agents and the judgment of the treating physician.

For pharmaceutical compositions that comprise a second therapeutic agent, an effective amount of the second therapeutic agent is between about 20% and 100% of the dosage normally utilized in a monotherapy regime using just that agent. Preferably, an effective amount is between about 70% and 100% of the normal monotherapeutic dose. The normal monotherapeutic dosages of these second therapeutic agents are well known in the art. See, e.g., Wells et al., eds., Pharmacotherapy Handbook, 2nd Edition, Appleton and Lange, Stamford, Conn. (2000); PDR Pharmacopoeia, Tarascon Pocket Pharmacopoeia 2000, Deluxe Edition, Tarascon Publishing, Loma Linda, Calif. (2000), each of which references are incorporated herein by reference in their entirety.

It is expected that some of the second therapeutic agents referenced above will act synergistically with the compounds of this invention. When this occurs, it will allow the effective dosage of the second therapeutic agent and/or the compound of this invention to be reduced from that required in a monotherapy. This has the advantage of minimizing toxic side effects of either the second therapeutic agent of a compound of this invention, synergistic improvements in efficacy, improved ease of administration or use and/or reduced overall expense of compound preparation or formulation.

Methods of Treatment

In another embodiment, the invention provides a method of potentiating the activity of CFTR in an infected cell, comprising contacting such a cell with a compound of Formula I herein, or a pharmaceutically acceptable salt thereof.

According to another embodiment, the invention provides a method of treating a disease that is beneficially treated by VX-770 in a subject in need thereof, comprising the step of administering to the subject an effective amount of a compound or a composition of this invention. In one embodiment the subject is a patient in need of such treatment. Such diseases include cystic fibrosis, Hereditary emphysema, Hereditary hemochromatosis, Coagulation-Fibrinolysis deficiencies, such as Protein C deficiency, Type 1 hereditary angioedema, Lipid processing deficiencies, such as Familial hypercholesterolemia, Type 1 chylomicronemia, Abetalipoproteinemia, Lysosomal storage diseases, such as I-cell disease/Pseudo-Hurler, Mucopolysaccharidoses, Sandhof/Tay-Sachs, Crigler-Najjar type II, Polyendocrinopathy/Hyperinsulemia, Diabetes mellitus, Laron dwarfism, Myleoperoxidase deficiency, Primary hypoparathyroidism, Melanoma, Glycanosis CDG type 1, Hereditary emphysema, Congenital hyperthyroidism, Osteogenesis imperfecta, Hereditary hypofibrinogenemia, ACT deficiency, Diabetes insipidus (DI), Neurophyseal DI, Neprogenic DI, Charcot-Marie Tooth syndrome, Perlizaeus-Merzbacher disease, neurodegenerative diseases such as Alzheimer's disease, Parkinson's disease, Amyotrophic lateral sclerosis, Progressive supranuclear palsy, Pick's disease, several polyglutamine neurological disorders such as Huntington, Spinocerebullar ataxia type I, Spinal and bulbar muscular atrophy, Dentatorubal pallidoluysian, and Myotonic dystrophy, as well as Spongiform encephalopathies, such as Hereditary Creutzfeldt-Jakob disease, Fabry disease, Straussler-Scheinker syndrome, COPD, dry-eye disease, and Sjogren's disease.

In one embodiment, a compound of this invention is used to treat cystic fibrosis in a subject such as a patient in need thereof. In one embodiment, a compound of this invention is used to treat COPD in a subject such as a patient in need thereof. In an example of either of the foregoing embodiments, the compound is administered by nasal aerosol or inhalation. In another example of either of the foregoing embodiments, the compound is administered orally.

In one embodiment, a compound of this invention is used to treat Parkinson's Disease in a subject such as a patient in need thereof.

In one embodiment, a compound of this invention is used to treat a bile duct disorder or a kidney ion channel disorder, including, but not limited to, Bartter's syndrome and Dent's disease in a subject such as a patient in need thereof.

In another embodiment, any of the above methods of treatment comprises the further step of co-administering to the subject in need thereof one or more second therapeutic agents. The choice of second therapeutic agent may be made from any second therapeutic agent known to be useful for co-administration with VX-770. The choice of second therapeutic agent is also dependent upon the particular disease or condition to be treated. Examples of second therapeutic agents that may be employed in the methods of this invention are those set forth above for use in combination compositions comprising a compound of this invention and a second therapeutic agent.

In particular, the combination therapies of this invention include co-administering a compound of Formula I or a pharmaceutically acceptable salt thereof and a second therapeutic agent such as VX-809 (lumacaftor) or VX-661, to a subject in need thereof for treatment.

The term "co-administered" as used herein means that the second therapeutic agent may be administered together with a compound of this invention as part of a single dosage form (such as a composition of this invention comprising a compound of the invention and an second therapeutic agent as described above) or as separate, multiple dosage forms. Alternatively, the additional agent may be administered prior to, consecutively with, or following the administration of a compound of this invention. In such combination therapy treatment, both the compounds of this invention and the second therapeutic agent(s) are administered by conventional methods. The administration of a composition of this invention, comprising both a compound of the invention and a second therapeutic agent, to a subject does not preclude the separate administration of that same therapeutic agent, any other second therapeutic agent or any compound of this invention to said subject at another time during a course of treatment.

Effective amounts of these second therapeutic agents are well known to those skilled in the art and guidance for dosing may be found in patents and published patent applications referenced herein, as well as in Wells et al., eds., Pharmacotherapy Handbook, 2nd Edition, Appleton and Lange, Stamford, Conn. (2000); PDR Pharmacopoeia, Tarascon Pocket Pharmacopoeia 2000, Deluxe Edition, Tarascon Publishing, Loma Linda, Calif. (2000), and other medical texts. However, it is well within the skilled artisan's purview to determine the second therapeutic agent's optimal effective-amount range.

In one embodiment of the invention, where a second therapeutic agent is administered to a subject, the effective amount of the compound of this invention is less than its effective amount would be where the second therapeutic agent is not administered. In another embodiment, the effective amount of the second therapeutic agent is less than its effective amount would be where the compound of this invention is not administered. In this way, undesired side effects associated with high doses of either agent may be minimized. Other potential advantages (including without limitation improved dosing regimens and/or reduced drug cost) will be apparent to those of skill in the art.

In yet another aspect, the invention provides the use of a compound of Formula I, or a pharmaceutically acceptable salt thereof, alone or together with one or more of the above-described second therapeutic agents in the manufacture of a medicament, either as a single composition or as separate dosage forms, for treatment or prevention in a subject of a disease, disorder or symptom set forth above. Another aspect of the invention is a compound of Formula I, or a pharmaceutically acceptable salt thereof, for use in the treatment or prevention in a subject of a disease, disorder or symptom thereof delineated herein.

EXAMPLES

Example 1. N-(3-Hydroxy-4-(2-(methyl-$d_3$)propan-2-yl-1,1,1,3,3,3-$d_6$)phenyl)-4-oxo-1,4-dihydroquinoline-3-carboxamide (Compound 100)

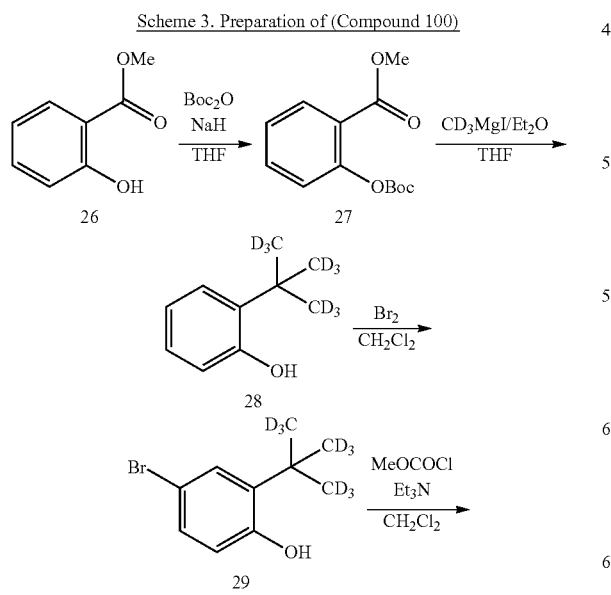

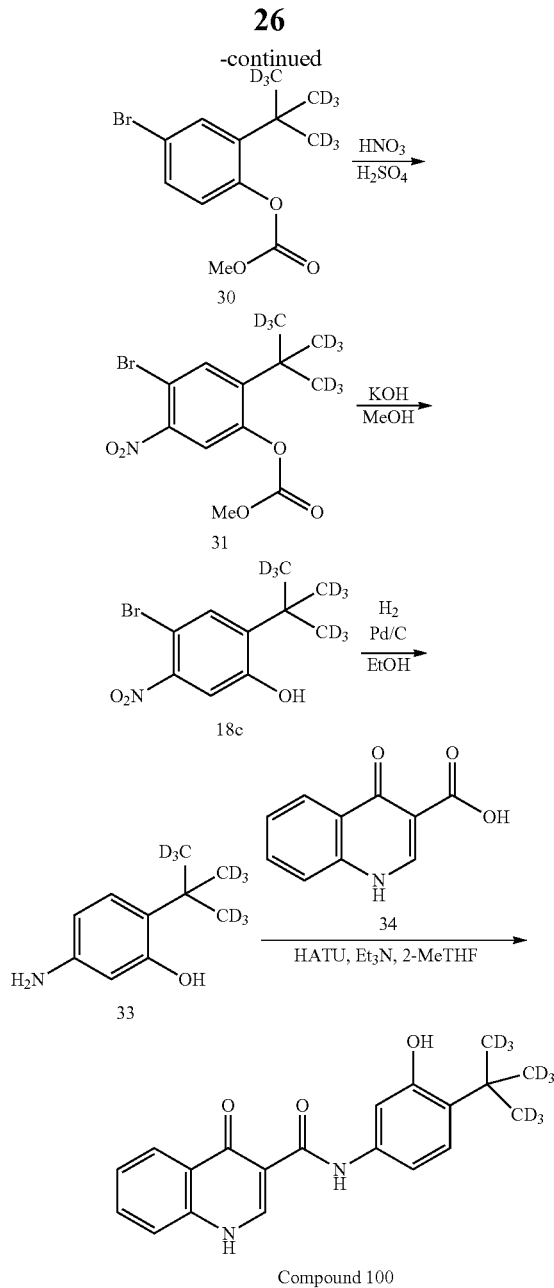

Step 1. Methyl 2-((tert-butoxycarbonyl)oxy)benzoate (27)

A solution of di-tert-butyldicarbonate (89.5 g, 410 mmol) in THF (50 mL) was added to a solution of methyl salicylate 26 (25.2 g, 165.6 mmol) in THF (300 mL) at 0° C. Sodium hydride (60% dispersion in mineral oil, 16.4 g, 410 mmol) was added over 5 minutes. The mixture was stirred at 0° C. for 30 minutes then at room temperature for 6 hours. The mixture was cooled to 0° C., diluted with MTBE (300 mL) and water (400 mL) was added. The layers were separated and the aqueous layer was extracted with MTBE (2×150 mL). The combined organic layer was washed with saturated sodium chloride (200 mL), dried over sodium sulfate, filtered and concentrated under reduced pressure. The resulting product was purified using an Analogix chromatography system (SiO$_2$, 0-10% ethyl acetate/heptanes) to afford 27 (39.2 g, 94% yield) as colorless oil.

Step 2. 2-(2-(Methyl-d$_3$)propan-2-yl-1,1,1,3,3,3-d$_6$) phenol (28)

A solution of 1.0M methyl-d$_3$-magnesium iodide in diethyl ether (260 mL, 260.0 mmol, 99 atom % D Sigma-Aldrich) was added over 15 minutes to a solution of 27 (18.77 g, 74.4 mmol) in THF (700 mL) at 0° C. with the reaction temperature rising to 22° C. during the addition. The mixture was stirred at 0° C. for 4 hours, then at room temperature overnight. The mixture was cooled to 0° C., quenched with IM aqueous hydrochloric acid (350 mL) and extracted with MTBE (500 mL, 300 mL, 200 mL). The combined organic layers were washed with saturated sodium chloride (300 mL), dried over sodium sulfate, filtered, and concentrated under reduced pressure. The resulting product was purified using an Analogix chromatography system (SiO$_2$, 0-10% ethyl acetate/heptanes) to afford 28 (7.19 g, 61% yield, ~70% purity) as yellow oil.

Step 3. 4-Bromo-2-(2-(methyl-d$_3$)propan-2-yl-1,1,1,3,3,3-d$_6$)phenol (29)

Bromine (2.3 mL, 44.9 mmol) was added dropwise to a solution of 28 (7.17 g, ~70% purity) in dichloromethane (70 mL) at 0° C. and the mixture was stirred at 0° C. for 40 minutes. Water (80 mL) was added and the mixture was extracted with dichloromethane (70 mL). The organic layer was washed with saturated aqueous sodium thiosulfate solution (2×50 mL) and saturated sodium chloride (2×30 mL), dried over sodium sulfate, filtered and concentrated under reduced pressure. The resulting product was purified using an Analogix chromatography system (SiO$_2$, 0-10% ethyl acetate/heptanes) to afford 29 (8.00 g, 75% yield, ~80% purity) as yellow oil.

Step 4. 4-Bromo-2-(2-(methyl-d$_3$)propan-2-yl-1,1,1,3,3,3-d$_6$)phenyl Methyl Carbonate (30)

Methylchloroformate (5.2 mL, 67.3 mmol) was added dropwise to a solution of 29 (8.00 g, ~80% purity) and triethylamine (6.6 mL, 47.3 mmol) in dichloromethane (150 mL) at 0° C. and the mixture was stirred at 0° C. for 2 hours. Saturated aqueous ammonium chloride (70 mL) was added, the layers were separated and the aqueous layer was extracted with dichloromethane (2×50 mL). The combined organic layer was washed with saturated sodium chloride (50 mL), dried over sodium sulfate, filtered and concentrated under reduced pressure. The resulting product was purified using an Analogix chromatography system (SiO$_2$, 0-10% ethyl acetate/heptanes) to afford 30 (7.36 g, 74% yield) as yellow oil.

Step 5. 4-Bromo-2-(2-(methyl-d$_3$)propan-2-yl-1,1,1,3,3,3-d$_6$)-5-nitrophenyl Methyl Carbonate (31)

A solution of 30 (12.90 g, 43.5 mmol) in dichloromethane (10 mL) was added to concentrated sulfuric acid (30 mL) at 0° C. Potassium nitrate (7.05 g, 69.7 mmol) was added in portions over 15 minutes at 0° C. The mixture was stirred at room temperature for 2 hours then cooled to 0° C. A mixture of ice and water (70 mL) was added and the mixture was extracted with dichloromethane (60 mL, 60 mL, 40 mL). The combined organic layer was dried over sodium sulfate, filtered and concentrated under reduced pressure. The resulting product was purified using an Analogix chromatography system (SiO$_2$, 0-15% ethyl acetate/heptanes) to give 31 (10.40 g, 70% yield) as a yellow solid.

Step 6. 4-Bromo-2-(2-(methyl-d$_3$)propan-2-yl-1,1,1,3,3,3-d$_6$)-5-nitrophenol (18c)

A solution of potassium hydroxide (2.56 g, 45.7 mmol) in methanol (50 mL) was added to a solution of 31 (10.40 g, 30.5 mmol) in dichloromethane (60 mL) and methanol (100 mL). The mixture was stirred at room temperature for 30 minutes then quenched with IM aqueous hydrochloric acid to pH 3. The mixture was concentrated under reduced pressure to remove methanol, and extracted with dichloromethane (3×70 mL). The combined organic layer was dried over sodium sulfate, filtered and concentrated under reduced pressure. The crude product was adsorbed onto Celite and the resulting product was purified using an Analogix chromatography system (SiO$_2$, 0-20% ethyl acetate/heptanes) to give 18c (8.00 g, 93% yield) as a bright yellow solid.

Step 7. 5-Amino-2-(2-(methyl-d$_3$)propan-2-yl-1,1,1,3,3,3-d$_6$)pheno(33)

Compound 18 (0.75 g, 2.65 mmol) was hydrogenated at 50 psi over 10% palladium on carbon (50% wet) (0.40 g) in ethanol (25 mL) overnight. The mixture was filtered through a pad of Celite, concentrated under reduced pressure and dry-loaded onto Celite. The resulting product was purified using an Analogix chromatography system (SiO$_2$, 0-50% ethyl acetate/heptanes, then 10% methanol/dichloromethane) to give 33 (0.46 g, quantitative yield) as an off-white solid.

Step 8. N-(3-Hydroxy-4-(2-(methyl-d$_3$)propan-2-yl-1,1,1,3,3,3-d$_6$)phenyl)-4-oxo-1,4-dihydroquinoline-3-carboxamide (Compound 100)

A mixture of 33 (0.26 g, 1.49 mmol), commercially available 34 (0.30 g, 1.58 mmol), HATU (0.62 g, 1.64 mmol) and triethylamine (0.46 mL, 3.28 mmol) in 2-methyltetrahydrofuran (20 mL) was heated at 70° C. for 6 hours. The mixture was diluted with THF (50 mL) and water (20 mL). The layers were separated and the aqueous layer was extracted with THF (2×20 mL). The combined organic layer was washed with saturated sodium chloride (10 mL), dried over sodium sulfate, filtered and concentrated under reduced pressure. The crude product was adsorbed onto Celite and purified using an Analogix chromatography system (SiO$_2$, 10-90% ethyl acetate/heptanes) to give titled compound (0.47 g). The material was triturated with diethyl ether (10 mL) for 30 minutes and filtered, washed with diethyl ether (20 mL), triturated with water (20 mL) for 30 minutes, filtered, washed with water (20 mL) and dried in a vacuum oven at 50° C. for 3 days to give Compound 100 (173 mg, 33% yield). 1H NMR (DMSO-d$_6$, 400 MHz) δ 12.8-12.9 (br s, 1H), 12.2-12.3 (s, 1H), 9.35-9.40 (s, 1H), 8.8-8.85 (s, 1H), 8.25-8.35 (d, 1H), 7.70-7.90 (m, 2H), 7.50-7.60 (m, 1H), 7.35-7.40 (s, 1H), 7.10-7.15 (m, 1H), 6.90-6.98 (m, 1H); 13C NMR (DMSO-d$_6$, 100 MHz) δ 176.8, 162.9, 156.5, 144.5, 139.6, 137.9, 131.2, 126.95, 126.4, 125.95, 125.7, 119.6, 111.2, 110.3, 108.1, 33.7; MS (ESI) 346.2 [(M+H)$^+$].

Example 2. N-(5-hydroxy-4-(2-(methyl-d₃)propan-2-yl-1,1,1,3,3,3-d₆)-2-(trifluoromethyl)phenyl)-4-oxo-1,4-dihydroquinoline-3-carboxamide (Compound 120)

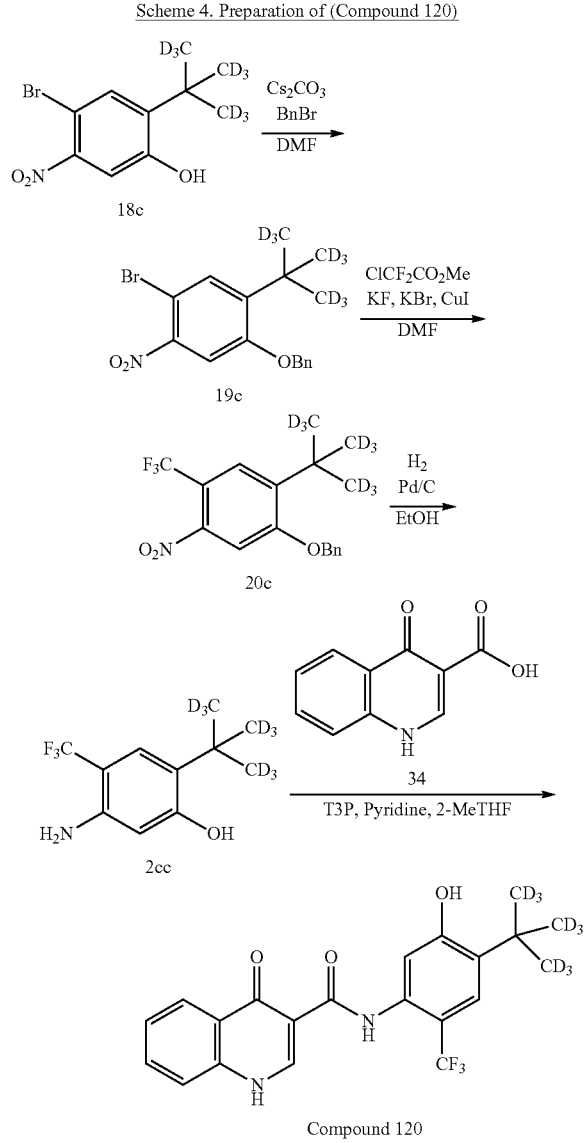

Step 1. 1-(Benzyloxy)-4-bromo-2-(2-(methyl-d₃)propan-2-yl-1,1,3,3,3-d₆)-5-nitrobenzene (19c)

Cesium carbonate (11.06 g, 33.9 mmol) was added in one portion to a solution of 18c (8.00 g, 28.3 mmol) in DMF (100 mL) followed by benzyl bromide (3.6 mL, 29.7 mmol). The mixture was stirred at room temperature overnight at which time LC-MS analysis indicated complete reaction. Water (100 mL) was added and the mixture was extracted with ethyl acetate (2×300 mL, 200 mL). The combined organic layer was washed with saturated sodium chloride (100 mL), dried over sodium sulfate, filtered, concentrated under reduced pressure, dry-loaded onto silica gel and the resulting product was purified using an Analogix chromatography system (SiO₂, 0-10% ethyl acetate/heptanes) to afford 19c (9.84 g, 93% yield) as a light yellow solid.

Step 2. 1-(Benzyloxy)-2-(2-(methyl-d₃)propan-2-yl-1,1,1,3,3,3-d₆)-5-nitro-4-(trifluoromethyl)benzene (20c)

A mixture of 19c (6.56 g, 17.6 mmol), potassium fluoride (2.04 g, 35.1 mmol), potassium bromide (4.18 g, 35.1 mmol), methyl chlorodifluoroacetate (16.0 mL, 151.7 mmol), and copper (I) iodide (4.00 g, 21.0 mmol) in DMF (40 mL) was heated overnight in a sealed tube at 120° C. (oil bath temperature). This reaction was repeated using 3.28 g (8.8 mmol) of 19c. The crude material was combined and water (100 mL) was added. The resulting mixture was extracted with ethyl acetate (2×300 mL, 200 mL), and the combined organic layer was washed with saturated sodium chloride (100 mL), dried over sodium sulfate, filtered, concentrated under reduced pressure, dry-loaded onto silica gel and was purified using an Interchim chromatography system (SiO₂, 0-10% ethyl acetate/heptanes) to give 20c (6.90 g, 72% yield, ~80% purity) as a light yellow solid.

Step 3. 5-Amino-2-(2-(methyl-d₃)propan-2-yl-1,1,1,3,3,3-d₆)-4-(trifluoromethyl)-phenol (2cc)

Compound 20c (6.90 g, 19.0 mmol, ~80% purity) was hydrogenated at 25 psi over 10% palladium on carbon (50 wt. % wet) (2.07 g)) in ethanol for 5 hours. The mixture was filtered through a Celite pad, concentrated under reduced pressure, dry-loaded onto Celite and was purified using an Analogix chromatography system (SiO₂, 0-20% ethyl acetate/heptanes) to give 2cc (1.46 g, 32% yield) as an off-white solid.

Step 4. N-(5-Hydroxy-4-(2-(methyl-d₃)propan-2-yl-1,1,1,3,3,3-d₆)-2-(trifluoromethyl)-phenyl)-4-oxo-1,4-dihydroquinoline-3-carboxamide (Compound 120)

A mixture of 2cc (0.79 g, 3.27 mmol), pyridine (0.53 mL, 6.5 mmol), commercially available 34 (0.65 g, 3.44 mmol), and ≥50 wt. % propylphosphonic anhydride solution in ethyl acetate (9.7 mL, 16.3 mmol) in 2-methyltetrahydrofuran (75 mL) was heated overnight at 50° C. The mixture was diluted with THF (50 mL), washed with saturated sodium bicarbonate solution (3×50 mL), saturated sodium chloride (30 mL), dried over sodium sulfate, filtered, concentrated under reduced pressure, and dry-loaded onto silica gel. The resulting product was purified using an Analogix chromatography system (SiO₂, 0-60% ethyl acetate/heptanes) to give Compound 120 (186 mg, 14% yield) as a white solid which was lyophilized from a mixture of methanol and benzene to remove residual solvents. 1H NMR (DMSO-d₆, 400 MHz) δ 12.85-13.0 (br s, 1H), 12.50-12.55 (s, 1H), 10.25-10.35 (s, 1H), 8.80-8.90 (s, 1H), 8.25-8.35 (d, 1H), 7.95-8.0 (s, 1H), 7.70-7.85 (m, 2H), 7.45-7.55 (s, 1H), 7.30-7.35 (m, 1H); 13C NMR (DMSO-d₆, 100 MHz) δ 176.8, 163.7, 159.8, 144.98, 139.6, 133.5, 131.5, 126.4, 126.1, 125.8, 119.7, 112.4, 110.7, 33.7; 19F (DMSO-d₆, 376 MHz) δ −57.99; MS (ESI) 414.2 [(M+H)⁺].

Compound A and Compound B, for use in Example 3 and 4 respectively, are prepared as described in U.S. Pat. No.

8,354,427 and Hadida, S. et al., Journal of Medicinal Chemistry, 57(23), 9776-9795; 2014.

Compound A. N-(4-(tert-butyl)-3-hydroxyphenyl)-4-oxo-1,4-dihydroquinoline-3-carboxamide Compound A

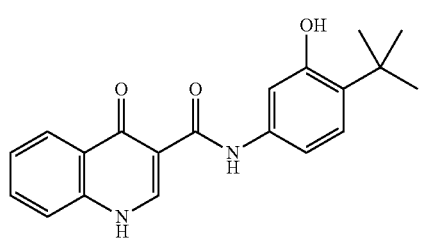

Compound B. N-(4-(tert-butyl)-5-hydroxy-2-(trifluoromethyl)phenyl)-4-oxo-1,4-dihydroquinoline-3-carboxamide Compound B

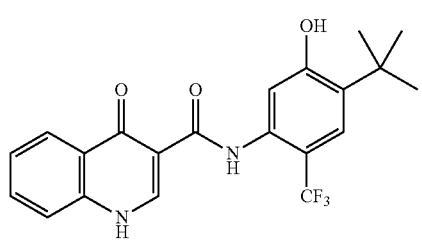

Example 3. Evaluation of Metabolic Stability of Compound 100 in Human CYP3A4 Supersomes™

SUPERSOMES™ Assay.

Stock solutions (7.5 mM) of Compound 100 and Compound A were prepared in DMSO. The 7.5 mM stock solutions were diluted to 12.5 µM in acetonitrile (ACN). The human CYP3A4 Supersomes™ (2000 pmol/mL, purchased from BD Biosciences™) were diluted to 62.5 pmol/mL in 0.1 M potassium phosphate buffer, pH 7.4, containing 3 mM MgCl$_2$. The diluted supersomes were added to wells of a 96-well polypropylene plate in triplicate. A 10 µL aliquot of the 12.5 µM test compound was added to the supersomes and the mixture was pre-warmed for 10 minutes. Reactions were initiated by addition of pre-warmed NADPH solution. The final reaction volume was 0.5 mL and contained 50 pmol/mL CYP3A4 Supersomes™, 0.25 µM test compound, and 2 mM NADPH in 0.1 M potassium phosphate buffer, pH 7.4, and 3 mM MgCl$_2$. The reaction mixtures were incubated at 37° C., and 50 µL aliquots were removed at 0, 3, 7, 10, 20 and 30 minutes and added to 96-well plates which contained 125 µL of ice-cold ACN with internal standard to stop the reactions. The plates were stored at 4° C. for 20 minutes after which 75 µL of water was added to the wells of the plate before centrifugation to pellet precipitated proteins. Supernatants were transferred to another 96-well plate and analyzed for amounts of parent remaining by LC-MS/MS using an AB Sciex QTrap 5500 mass spectrometer.

Data Analysis:

The in vitro half-lives ($t_{1/2}$ values) for test compounds were calculated from the slopes of the linear regression of LN (% parent remaining) vs incubation time relationship:

in vitro $t_{1/2}$=0.693/k, where k=−[slope of linear regression of LN (% parent remaining) vs incubation time].

The results of this experiment are shown in Table 2, below. Compound 100 was shown to be more stable in Human CYP3A4 Supersomes™ relative to Compound A, with a calculated average half-life of 26.5 minutes for Compound 100 and 15.1 minutes for Compound A. This represents an average 75% increase in $t_{1/2}$ for Compound 100 and an apparent intrinsic clearance ratio of 0.57 µL/min*pmol.

TABLE 2

Metabolic Stability of Compound 100 versus Compound A in Human CYP3A4 Supersomes ™

| Compound | *$t_{1/2}$ (minutes) | **$Cl_{int, app}$ rCYP (µL/min*pmol) Ratio (100/A) |
|---|---|---|
| Compound A | 15.1 ± 0.69 | 0.46 ± 0.02 |
| Compound 100 | 26.5 ± 1.4 | 0.26 ± 0.00 |

*$t_{1/2}$ was calculated based on 10 min data;
** CL int = (0.693/In Vitro T½) (mL IncubationVolume/pmol P450)

Example 4. Evaluation of Metabolic Stability of Compound 120 in Human CYP3A4. Supersomes™

SUPERSOMES™ Assay.

Stock solutions (7.5 mM) of Compound 120 and Compound B were prepared in DMSO. The 7.5 mM stock solutions were diluted to 12.5 µM in acetonitrile (ACN). The human CYP3A4 Supersomes™ (2000 pmol/mL, purchased from BD Biosciences™) were diluted to 62.5 pmol/mL in 0.1 M potassium phosphate buffer, pH 7.4, containing 3 mM MgCl$_2$. The diluted supersomes were added to wells of a 96-well polypropylene plate in triplicate. A 10 µL aliquot of the 12.5 µM test compound was added to the supersomes and the mixture was pre-warmed for 10 minutes. Reactions were initiated by addition of pre-warmed NADPH solution. The final reaction volume was 0.5 mL and contained 50 pmol/mL CYP3A4 Supersomes™, 0.25 µM test compound, and 2 mM NADPH in 0.1 M potassium phosphate buffer, pH 7.4, and 3 mM MgCl$_2$. The reaction mixtures were incubated at 37° C., and 50 µL aliquots were removed at 0, 3, 7, 10, 20 and 30 minutes and added to 96-well plates which contained 125 µL of ice-cold ACN with internal standard to stop the reactions. The plates were stored at 4° C. for 20 minutes after which 75 µL of water was added to the wells of the plate before centrifugation to pellet precipitated proteins. Supernatants were transferred to another 96-well plate and analyzed for amounts of parent remaining by LC-MS/MS using an AB Sciex QTrap 5500 mass spectrometer.

Data Analysis:

The in vitro half-lives ($t_{1/2}$ values) for test compounds were calculated from the slopes of the linear regression of LN (% parent remaining) vs incubation time relationship:

in vitro $t_{1/2}$=0.693/k, where k=−[slope of linear regression of LN (% parent remaining) vs incubation time].

The results of this experiment are shown in Table 3. Compound 120 was shown to be more stable in Human CYP3A4 Supersomes™ relative to Compound B, with a calculated average half-life of 20.6 minutes for Compound 120 and 14.5 minutes for Compound B. This represents an average 42% increase in $t_{1/2}$ for compound 120 and an apparent intrinsic clearance ratio of 0.71 mL/min*pmol.

TABLE 3

Metabolic Stability of Compound 120 versus Compound B in Human CYP3A4 Supersomes™

| Compound | *$t_{1/2}$ (minutes) (% Δ) | **$Cl_{int, app}$ rCYP (μL/min*pmol) Ratio (120/B) |
|---|---|---|
| Compound B | 14.5 ± 1.8 | 0.48 ± 0.06 |
| Compound 120 | 20.6 ± 2.7 | 0.34 ± 0.00 |

*$t_{1/2}$ was calculated based on 10 min data;
**CL int = (0.693 / In Vitro T½) (mL Incubation Volume/pmol P450)

Data analysis was performed using Microsoft Excel Software.

Without further description, it is believed that one of ordinary skill in the art can, using the preceding description and the illustrative examples, make and utilize the compounds of the present invention and practice the claimed methods. It should be understood that the foregoing discussion and examples merely present a detailed description of certain preferred embodiments. It will be apparent to those of ordinary skill in the art that various modifications and equivalents can be made without departing from the spirit and scope of the invention.

We claim:

1. A process for the synthesis of compound 28:

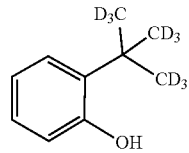

28 comprising converting compound 27:

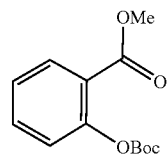

27 into compound 28 in the presence of —$CD_3MgI$, diethyl ether, and THF.

* * * * *

UNITED STATES PATENT AND TRADEMARK OFFICE
CERTIFICATE OF CORRECTION

PATENT NO. : 10,759,721 B2  
APPLICATION NO. : 15/762264  
DATED : September 1, 2020  
INVENTOR(S) : Adam J. Morgan et al.

Page 1 of 1

It is certified that error appears in the above-identified patent and that said Letters Patent is hereby corrected as shown below:

Claim 1, Column 34, Line 27, "—CD$_3$MgI" should read as --CD$_3$MgI--.

Signed and Sealed this  
Eighth Day of December, 2020

Andrei Iancu  
*Director of the United States Patent and Trademark Office*